US011676694B2

(12) United States Patent
Kruse et al.

(10) Patent No.: US 11,676,694 B2
(45) Date of Patent: Jun. 13, 2023

(54) DEVICE AND METHOD FOR TRAINING USERS OF AMBULATORY MEDICAL DEVICES

(71) Applicant: Tandem Diabetes Care, Inc., San Diego, CA (US)

(72) Inventors: Geoffrey A. Kruse, San Diego, CA (US); Kim Blickenstaff, San Diego, CA (US); Michael J. Rosinko, Anaheim, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 484 days.

(21) Appl. No.: 16/846,908

(22) Filed: Apr. 13, 2020

(65) Prior Publication Data

US 2020/0254174 A1 Aug. 13, 2020

Related U.S. Application Data

(63) Continuation of application No. 15/808,286, filed on Nov. 9, 2017, now Pat. No. 10,653,834, which is a
(Continued)

(51) Int. Cl.
*A61M 5/172* (2006.01)
*G16H 20/17* (2018.01)
(Continued)

(52) U.S. Cl.
CPC .......... *G16H 20/17* (2018.01); *A61M 5/1413* (2013.01); *A61M 5/14244* (2013.01);
(Continued)

(58) Field of Classification Search
CPC ........ A61M 2205/502; A61M 2205/52; A61M 2230/201; A61M 5/1723; A61M 2205/505; A61M 2230/005
See application file for complete search history.

(56) References Cited

U.S. PATENT DOCUMENTS 80,576 A 8/1868 Yu et al.
2,462,596 A 2/1949 Bent
(Continued)

FOREIGN PATENT DOCUMENTS

CA 2930776 C 5/2018
DE 399065 C 7/1924
(Continued)

OTHER PUBLICATIONS

US 8,333,733 B2, 12/2012, Lanigan et al. (withdrawn)
(Continued)

*Primary Examiner* — Deanna K Hall
(74) *Attorney, Agent, or Firm* — Patterson Thuente IP

(57) ABSTRACT

Apparatuses and methods for training users of ambulatory medical devices. The methods relate to improving user interactions with the touchscreens of devices. In one embodiment there is an operating mode that records all user interactions along with various device parameters and allows the clinician to review the patient's performance for the initial use period. Automated analysis software may be employed to analyze the data generated by the device. The results of the analysis may be used by the clinician to improve the patient and device interaction.

20 Claims, 6 Drawing Sheets

Related U.S. Application Data continuation of application No. 14/992,709, filed on Jan. 11, 2016, now Pat. No. 9,814,835, which is a continuation of application No. 13/828,958, filed on Mar. 14, 2013, now Pat. No. 9,238,100.

(60) Provisional application No. 61/656,984, filed on Jun. 7, 2012.

(51) Int. Cl.
    *A61M 5/14*        (2006.01)
    *A61M 5/142*       (2006.01)

(52) U.S. Cl.
    CPC .......... *A61M 5/172* (2013.01); *A61M 5/1723* (2013.01); *A61M 2205/502* (2013.01); *A61M 2205/505* (2013.01); *A61M 2205/52* (2013.01); *A61M 2230/005* (2013.01); *A61M 2230/201* (2013.01)

(56) References Cited

U.S. PATENT DOCUMENTS

| | | |
|---|---|---|
| 2,629,376 A | 2/1953 | Pierre et al. |
| 2,691,542 A | 10/1954 | Chenoweth |
| 3,059,639 A | 10/1962 | Blackman et al. |
| 3,189,125 A | 6/1965 | Windsor et al. |
| 3,227,311 A | 1/1966 | Rowell |
| 3,847,178 A | 11/1974 | Keppel |
| 4,392,849 A | 7/1983 | Petre et al. |
| 4,393,365 A | 7/1983 | Kondo et al. |
| 4,475,901 A | 10/1984 | Kraegen et al. |
| 4,492,339 A | 1/1985 | Kreitzberg |
| 4,529,401 A | 7/1985 | Leslie et al. |
| 4,741,736 A | 5/1988 | Brown |
| 5,000,664 A | 3/1991 | Lawless et al. |
| 5,050,612 A | 9/1991 | Matsumura |
| 5,122,362 A | 6/1992 | Phillips et al. |
| 5,131,816 A | 7/1992 | Brown et al. |
| 5,153,827 A | 10/1992 | Coutre et al. |
| 5,181,910 A | 1/1993 | Scanlon |
| 5,207,666 A | 5/1993 | Idriss et al. |
| 5,219,330 A | 6/1993 | Bollish et al. |
| 5,240,603 A | 8/1993 | Frank et al. |
| 5,247,434 A | 9/1993 | Peterson et al. |
| 5,311,175 A | 5/1994 | Waldman |
| 5,322,626 A | 6/1994 | Frank et al. |
| 5,338,157 A | 8/1994 | Blomquist |
| 5,356,379 A | 10/1994 | Vaillancourt |
| 5,364,346 A | 11/1994 | Schrezenmeir |
| 5,368,562 A | 11/1994 | Blomquist et al. |
| 5,376,070 A | 12/1994 | Purvis et al. |
| 5,389,078 A | 2/1995 | Zalesky et al. |
| 5,464,392 A | 11/1995 | Epstein et al. |
| 5,478,211 A | 12/1995 | Dominiak |
| 5,482,446 A | 1/1996 | Williamson et al. |
| 5,485,408 A | 1/1996 | Blomquist |
| 5,497,772 A | 3/1996 | Schulman et al. |
| 5,522,798 A | 6/1996 | Johnson et al. |
| 5,551,850 A | 9/1996 | Williamson et al. |
| 5,558,638 A | 9/1996 | Evers et al. |
| 5,569,186 A | 10/1996 | Lord et al. |
| 5,582,593 A | 12/1996 | Hultman |
| 5,658,250 A | 8/1997 | Blomquist et al. |
| 5,658,252 A | 8/1997 | Johnson |
| 5,660,163 A | 8/1997 | Schulman et al. |
| 5,665,065 A | 9/1997 | Colman et al. |
| 5,669,877 A | 9/1997 | Blomquist |
| 5,681,285 A | 10/1997 | Ford et al. |
| 5,685,844 A | 11/1997 | Marttila |
| 5,695,473 A | 12/1997 | Olsen |
| 5,713,856 A | 2/1998 | Eggers et al. |
| 5,718,562 A | 2/1998 | Lawless et al. |
| 5,719,761 A | 2/1998 | Gatti et al. |
| 5,728,396 A | 3/1998 | Peery et al. |
| 5,745,378 A | 4/1998 | Barker et al. |
| 5,770,149 A | 6/1998 | Raible |
| 5,779,122 A | 7/1998 | Martinelli |
| 5,782,805 A | 7/1998 | Meinzer et al. |
| 5,795,327 A | 8/1998 | Wilson et al. |
| 5,807,336 A | 9/1998 | Russo et al. |
| 5,810,771 A | 9/1998 | Blomquist |
| 5,814,015 A | 9/1998 | Gargano et al. |
| 5,822,715 A | 10/1998 | Worthington et al. |
| 5,823,746 A | 10/1998 | Johnson |
| 5,837,220 A | 11/1998 | Blake et al. |
| 5,863,187 A | 1/1999 | Bensley et al. |
| 5,876,370 A | 3/1999 | Blomquist |
| 5,879,143 A | 3/1999 | Cote et al. |
| 5,885,211 A | 3/1999 | Eppstein et al. |
| 5,919,209 A | 7/1999 | Schouten |
| 5,935,099 A | 8/1999 | Peterson et al. |
| 5,935,106 A | 8/1999 | Olsen |
| 5,960,403 A | 9/1999 | Brown |
| 5,985,305 A | 11/1999 | Peery et al. |
| 6,023,629 A | 2/2000 | Tamada |
| 6,024,539 A | 2/2000 | Blomquist |
| 6,024,699 A | 2/2000 | Surwit et al. |
| 6,053,887 A | 4/2000 | Levitas et al. |
| 6,077,055 A | 6/2000 | Vilks |
| 6,093,172 A | 7/2000 | Funderburk et al. |
| RE36,871 E | 9/2000 | Epstein et al. |
| 6,120,460 A | 9/2000 | Abreu |
| 6,122,536 A | 9/2000 | Sun et al. |
| 6,135,949 A | 10/2000 | Russo et al. |
| 6,142,939 A | 11/2000 | Eppstein et al. |
| 6,144,869 A | 11/2000 | Berner et al. |
| 6,175,752 B1 | 1/2001 | Say et al. |
| 6,179,583 B1 | 1/2001 | Weston |
| 6,198,383 B1 | 3/2001 | Sekura et al. |
| 6,231,560 B1 | 5/2001 | Bui et al. |
| 6,233,471 B1 | 5/2001 | Berner et al. |
| 6,241,704 B1 | 6/2001 | Peterson et al. |
| 6,248,057 B1 | 6/2001 | Mavity et al. |
| 6,248,067 B1 | 6/2001 | Causey, III et al. |
| 6,249,717 B1 | 6/2001 | Nicholson et al. |
| 6,270,478 B1 | 8/2001 | Mern.o slashed.e |
| 6,272,364 B1 | 8/2001 | Kurnik |
| 6,298,254 B2 | 10/2001 | Tamada |
| 6,306,420 B1 | 10/2001 | Cheikh |
| 6,358,225 B1 | 3/2002 | Butterfield |
| 6,360,888 B1 | 3/2002 | McIvor et al. |
| 6,368,272 B1 | 4/2002 | Porumbescu |
| 6,379,301 B1 | 4/2002 | Worthington et al. |
| 6,395,292 B2 | 5/2002 | Peery et al. |
| 6,422,057 B1 | 7/2002 | Anderson |
| 6,424,847 B1 | 7/2002 | Mastrototaro et al. |
| 6,427,088 B1 | 7/2002 | Bowman, IV et al. |
| 6,438,408 B1 | 8/2002 | Mulligan et al. |
| 6,458,256 B1 | 10/2002 | Zhong |
| 6,467,267 B2 | 10/2002 | Kanazawa et al. |
| 6,468,242 B1 | 10/2002 | Wilson et al. |
| 6,470,234 B1 | 10/2002 | McGrady |
| 6,475,180 B2 | 11/2002 | Peterson et al. |
| 6,475,750 B1 | 11/2002 | Han et al. |
| 6,505,059 B1 | 1/2003 | Kollias et al. |
| 6,514,689 B2 | 2/2003 | Han et al. |
| 6,517,482 B1 | 2/2003 | Elden et al. |
| 6,535,714 B2 | 3/2003 | Melker et al. |
| 6,539,250 B1 | 3/2003 | Bettinger |
| 6,544,212 B2 | 4/2003 | Galley et al. |
| 6,544,229 B1 | 4/2003 | Danby et al. |
| 6,546,269 B1 | 4/2003 | Kurnik |
| 6,551,276 B1 | 4/2003 | Mann et al. |
| 6,553,244 B2 | 4/2003 | Lesho et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,558,902 B1 | 5/2003 | Hillenkamp |
| 6,562,001 B2 | 5/2003 | Lebel et al. |
| 6,564,104 B2 | 5/2003 | Nelson et al. |
| 6,565,509 B1 | 5/2003 | Say et al. |
| 6,571,128 B2 | 5/2003 | Lebel et al. |
| 6,577,899 B2 | 6/2003 | Lebel et al. |

(56) References Cited

U.S. PATENT DOCUMENTS

| | | |
|---|---|---|
| 6,582,366 B1 | 6/2003 | Porumbescu |
| 6,587,705 B1 | 7/2003 | Kim et al. |
| 6,589,229 B1 | 7/2003 | Connelly et al. |
| 6,594,514 B2 | 7/2003 | Berner et al. |
| 6,595,919 B2 | 7/2003 | Berner et al. |
| 6,623,698 B2 | 9/2003 | Kuo |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,653,091 B1 | 11/2003 | Dunn et al. |
| 6,656,114 B1 | 12/2003 | Poulsen et al. |
| 6,656,158 B2 | 12/2003 | Mahoney et al. |
| 6,656,159 B2 | 12/2003 | Flaherty |
| 6,659,978 B1 | 12/2003 | Kasuga et al. |
| 6,666,665 B1 | 12/2003 | Nguyen et al. |
| 6,668,196 B1 | 12/2003 | Villegas et al. |
| 6,669,669 B2 | 12/2003 | Flaherty et al. |
| 6,687,522 B2 | 2/2004 | Tamada |
| 6,692,457 B2 | 2/2004 | Flaherty |
| 6,694,191 B2 | 2/2004 | Starkweather et al. |
| 6,699,218 B2 | 3/2004 | Flaherty et al. |
| 6,723,072 B2 | 4/2004 | Flaherty et al. |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,152 B2 | 6/2004 | Kroll |
| 6,744,350 B2 | 6/2004 | Blomquist |
| 6,749,587 B2 | 6/2004 | Flaherty |
| 6,768,425 B2 | 7/2004 | Flaherty et al. |
| 6,771,250 B1 | 8/2004 | Oh |
| 6,773,412 B2 | 8/2004 | O'Mahony et al. |
| 6,790,198 B1 | 9/2004 | White et al. |
| 6,796,956 B2 | 9/2004 | Hartlaub et al. |
| 6,801,420 B2 | 10/2004 | Talbot et al. |
| 6,805,687 B2 | 10/2004 | Dextradeur et al. |
| 6,809,563 B2 | 10/2004 | Schaal |
| 6,809,653 B1 | 10/2004 | Mann et al. |
| 6,810,290 B2 | 10/2004 | Lebel et al. |
| 6,821,249 B2 | 11/2004 | Casscells, III et al. |
| 6,830,558 B2 | 12/2004 | Flaherty et al. |
| 6,835,175 B1 | 12/2004 | Porumbescu |
| 6,850,252 B1 | 2/2005 | Hoffberg |
| 6,852,104 B2 | 2/2005 | Blomquist |
| 6,872,200 B2 | 3/2005 | Mann et al. |
| 6,873,268 B2 | 3/2005 | Lebel et al. |
| 6,880,564 B2 | 4/2005 | Erickson |
| 6,882,940 B2 | 4/2005 | Potts et al. |
| 6,886,556 B2 | 5/2005 | Fuchs |
| 6,895,263 B2 | 5/2005 | Shin et al. |
| 6,902,905 B2 | 6/2005 | Burson et al. |
| 6,928,338 B1 | 8/2005 | Buchser et al. |
| 6,934,220 B1 | 8/2005 | Cruitt et al. |
| 6,936,029 B2 | 8/2005 | Mann et al. |
| 6,949,081 B1 | 9/2005 | Chance |
| 6,950,708 B2 | 9/2005 | Bowman, IV et al. |
| 6,953,323 B2 | 10/2005 | Childers et al. |
| 6,957,655 B2 | 10/2005 | Erickson et al. |
| 6,958,705 B2 | 10/2005 | Lebel et al. |
| 6,960,192 B1 | 11/2005 | Flaherty et al. |
| 6,966,325 B2 | 11/2005 | Erickson |
| 6,970,742 B2 | 11/2005 | Mann et al. |
| 6,974,437 B2 | 12/2005 | Lebel et al. |
| 6,979,326 B2 | 12/2005 | Mann et al. |
| 6,997,920 B2 | 2/2006 | Mann et al. |
| 6,998,387 B1 | 2/2006 | Goke et al. |
| 6,999,810 B2 | 2/2006 | Berner et al. |
| 6,999,854 B2 | 2/2006 | Roth |
| 7,004,928 B2 | 2/2006 | Aceti et al. |
| 7,008,413 B2 | 3/2006 | Kovach et al. |
| 7,011,630 B2 | 3/2006 | Desai et al. |
| 7,015,782 B2 | 3/2006 | Kincaid et al. |
| 7,018,360 B2 | 3/2006 | Flaherty et al. |
| 7,025,743 B2 | 4/2006 | Mann et al. |
| 7,029,455 B2 | 4/2006 | Flaherty |
| 7,031,772 B2 | 4/2006 | Condie et al. |
| 7,033,338 B2 | 4/2006 | Vilks et al. |
| 7,041,082 B2 | 5/2006 | Blomquist et al. |
| 7,053,761 B2 | 5/2006 | Schofield et al. |
| 7,056,179 B2 | 6/2006 | Courtney |
| 7,092,796 B2 | 8/2006 | Vanderveen |
| 7,098,803 B2 | 8/2006 | Mann et al. |
| 7,107,706 B1 | 9/2006 | Bailey, Sr. et al. |
| 7,109,878 B2 | 9/2006 | Mann et al. |
| 7,128,727 B2 | 10/2006 | Flaherty et al. |
| 7,137,964 B2 | 11/2006 | Flaherty |
| 7,144,384 B2 | 12/2006 | Gorman et al. |
| 7,150,741 B2 | 12/2006 | Erickson et al. |
| 7,174,199 B2 | 2/2007 | Berner et al. |
| 7,179,226 B2 | 2/2007 | Crothall et al. |
| 7,181,505 B2 | 2/2007 | Haller et al. |
| 7,183,068 B2 | 2/2007 | Burson et al. |
| 7,187,528 B2 | 3/2007 | Talbot et al. |
| 7,193,521 B2 | 3/2007 | Moberg et al. |
| 7,204,823 B2 | 4/2007 | Estes et al. |
| 7,229,288 B2 | 6/2007 | Stuart et al. |
| 7,231,263 B2 | 6/2007 | Choi |
| 7,232,435 B2 | 6/2007 | Hildebrand et al. |
| 7,247,702 B2 | 7/2007 | Gardner et al. |
| 7,264,730 B2 | 9/2007 | Connell et al. |
| 7,267,665 B2 | 9/2007 | Steil et al. |
| 7,278,983 B2 | 10/2007 | Ireland et al. |
| 7,282,029 B1 | 10/2007 | Poulsen et al. |
| 7,291,107 B2 | 11/2007 | Hellwig et al. |
| 7,295,867 B2 | 11/2007 | Berner et al. |
| 7,303,549 B2 | 12/2007 | Flaherty et al. |
| 7,303,680 B2 | 12/2007 | Connell et al. |
| 7,307,245 B2 | 12/2007 | Faries, Jr. et al. |
| 7,318,892 B2 | 1/2008 | Connell et al. |
| 7,324,012 B2 | 1/2008 | Mann et al. |
| 7,341,577 B2 | 3/2008 | Gill |
| 7,351,340 B2 | 4/2008 | Connell et al. |
| 7,354,420 B2 | 4/2008 | Steil et al. |
| 7,384,410 B2 | 6/2008 | Eggers et al. |
| 7,385,443 B1 | 6/2008 | Denison |
| 7,390,311 B2 | 6/2008 | Hildebrand et al. |
| 7,390,458 B2 | 6/2008 | Burow et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,405,055 B2 | 7/2008 | Dunn et al. |
| 7,445,616 B2 | 11/2008 | Petrakis |
| 7,446,091 B2 | 11/2008 | Van Den Berghe |
| 7,460,350 B2 | 12/2008 | Talbot et al. |
| 7,465,375 B2 | 12/2008 | Demers et al. |
| 7,469,383 B2 | 12/2008 | Busch |
| 7,471,994 B2 | 12/2008 | Ford et al. |
| 7,483,743 B2 | 1/2009 | Mann et al. |
| 7,491,187 B2 | 2/2009 | Van Den Berghe et al. |
| 7,497,827 B2 | 3/2009 | Brister et al. |
| 7,514,075 B2 | 4/2009 | Hedrick et al. |
| 7,515,060 B2 | 4/2009 | Blomquist |
| 7,524,287 B2 | 4/2009 | Bharmi |
| 7,553,281 B2 | 6/2009 | Hellwig et al. |
| 7,556,613 B2 | 7/2009 | Wittmann et al. |
| 7,559,926 B1 | 7/2009 | Blischak |
| 7,588,046 B1 | 9/2009 | Erickson |
| 7,590,443 B2 | 9/2009 | Bharmi |
| 7,591,801 B2 | 9/2009 | Brauker et al. |
| 7,594,889 B2 | 9/2009 | St. Ores et al. |
| 7,602,310 B2 | 10/2009 | Mann et al. |
| 7,621,893 B2 | 11/2009 | Moberg et al. |
| 7,647,237 B2 | 1/2010 | Malave et al. |
| 7,651,489 B2 | 1/2010 | Estes et al. |
| 7,651,845 B2 | 1/2010 | Doyle, III et al. |
| 7,668,731 B2 | 2/2010 | Martucci et al. |
| 7,674,485 B2 | 3/2010 | Bhaskaran et al. |
| 7,678,071 B2 | 3/2010 | Lebel et al. |
| 7,678,762 B2 | 3/2010 | Green et al. |
| 7,678,763 B2 | 3/2010 | Green et al. |
| 7,687,272 B1 | 3/2010 | Buchwald et al. |
| 7,699,775 B2 | 4/2010 | Desai et al. |
| 7,704,226 B2 | 4/2010 | Mueller, Jr. et al. |
| 7,711,402 B2 | 5/2010 | Shults et al. |

(56) References Cited

U.S. PATENT DOCUMENTS

| | | |
|---|---|---|
| 7,714,757 B2 | 5/2010 | Denison et al. |
| 7,715,893 B2 | 5/2010 | Kamath et al. |
| 7,715,917 B2 | 5/2010 | Chinchoy et al. |
| 7,717,903 B2 | 5/2010 | Estes et al. |
| 7,734,323 B2 | 6/2010 | Blomquist et al. |
| 7,751,907 B2 | 7/2010 | Blomquist |
| 7,766,829 B2 | 8/2010 | Sloan et al. |
| 7,766,873 B2 | 8/2010 | Moberg et al. |
| 7,768,386 B2 | 8/2010 | Hayter et al. |
| 7,768,408 B2 | 8/2010 | Reggiardo et al. |
| 7,774,038 B2 | 8/2010 | Wang et al. |
| 7,774,145 B2 | 8/2010 | Brauker et al. |
| 7,776,031 B2 | 8/2010 | Hartlaub et al. |
| 7,785,313 B2 | 8/2010 | Mastrototaro |
| 7,801,582 B2 | 9/2010 | Peyser |
| 7,806,853 B2 | 10/2010 | Wittmann et al. |
| 7,806,886 B2 | 10/2010 | Kanderian, Jr. et al. |
| 7,811,279 B2 | 10/2010 | John |
| 7,815,602 B2 | 10/2010 | Mann et al. |
| 7,819,843 B2 | 10/2010 | Mann et al. |
| 7,831,310 B2 | 11/2010 | Lebel et al. |
| 7,837,647 B2 | 11/2010 | Estes et al. |
| 7,860,583 B2 | 12/2010 | Condurso et al. |
| 7,869,851 B2 | 1/2011 | Hellwig et al. |
| 7,875,022 B2 | 1/2011 | Wenger et al. |
| 7,879,026 B2 | 2/2011 | Estes et al. |
| 7,884,729 B2 | 2/2011 | Reggiardo et al. |
| 7,887,505 B2 | 2/2011 | Flaherty |
| 7,890,295 B2 | 2/2011 | Shin et al. |
| 7,892,206 B2 | 2/2011 | Moberg et al. |
| 7,896,704 B2 | 3/2011 | Stafford et al. |
| 7,912,674 B2 | 3/2011 | Killoren Clark et al. |
| 7,914,499 B2 | 3/2011 | Gonnelli et al. |
| 7,920,907 B2 | 4/2011 | McGarraugh et al. |
| 7,922,458 B2 | 4/2011 | Rush et al. |
| 7,922,899 B2 | 4/2011 | Vasta et al. |
| 7,935,076 B2 | 5/2011 | Estes et al. |
| 7,935,104 B2 | 5/2011 | Yodfat et al. |
| 7,935,499 B2 | 5/2011 | Dunn et al. |
| 7,938,792 B2 | 5/2011 | Roger et al. |
| 7,938,797 B2 | 5/2011 | Estes |
| 7,941,200 B2 | 5/2011 | Weinert et al. |
| 7,942,844 B2 | 5/2011 | Moberg et al. |
| 7,946,985 B2 | 5/2011 | Mastrototaro et al. |
| 7,955,295 B2 | 6/2011 | Lee et al. |
| 7,959,598 B2 | 6/2011 | Estes |
| 7,963,946 B2 | 6/2011 | Moubayed et al. |
| 7,967,773 B2 | 6/2011 | Amborn et al. |
| 7,972,296 B2 | 7/2011 | Braig et al. |
| 7,976,492 B2 | 7/2011 | Brauker et al. |
| 7,979,136 B2 | 7/2011 | Young et al. |
| 7,981,034 B2 | 7/2011 | Jennewine et al. |
| 7,985,330 B2 | 7/2011 | Wang et al. |
| 7,988,660 B2 | 8/2011 | Byland et al. |
| 7,988,849 B2 | 8/2011 | Biewer et al. |
| 7,988,850 B2 | 8/2011 | Roncadi et al. |
| 7,991,625 B2 | 8/2011 | Rosenfeld et al. |
| 7,991,627 B2 | 8/2011 | Hutchinson et al. |
| 7,993,108 B2 | 8/2011 | Rush et al. |
| 7,996,158 B2 | 8/2011 | Hayter et al. |
| 7,998,111 B2 | 8/2011 | Moberg et al. |
| 7,999,674 B2 | 8/2011 | Kamen |
| 8,005,524 B2 | 8/2011 | Brauker et al. |
| 8,012,119 B2 | 9/2011 | Estes et al. |
| 8,025,634 B1 | 9/2011 | Moubayed et al. |
| 8,029,245 B2 | 10/2011 | Rush et al. |
| 8,029,250 B2 | 10/2011 | Rush et al. |
| 8,029,459 B2 | 10/2011 | Rush et al. |
| 8,029,460 B2 | 10/2011 | Rush et al. |
| 8,030,891 B2 | 10/2011 | Welsch et al. |
| 8,032,226 B2 | 10/2011 | Miller et al. |
| 8,034,026 B2 | 10/2011 | Grant et al. |
| 8,047,811 B2 | 11/2011 | Rush et al. |
| 8,047,812 B2 | 11/2011 | Rush et al. |
| 8,060,185 B2 | 11/2011 | Hunter et al. |
| 8,062,249 B2 | 11/2011 | Wilinska et al. |
| 8,062,257 B2 | 11/2011 | Moberg et al. |
| 8,062,513 B2 | 11/2011 | Yu et al. |
| 8,065,096 B2 | 11/2011 | Moberg et al. |
| 8,066,665 B2 | 11/2011 | Rush et al. |
| 8,070,742 B2 | 12/2011 | Woo |
| 8,075,527 B2 | 12/2011 | Rush et al. |
| 8,079,983 B2 | 12/2011 | Rush et al. |
| 8,079,984 B2 | 12/2011 | Rush et al. |
| 8,083,718 B2 | 12/2011 | Rush et al. |
| 8,088,098 B2 | 1/2012 | Yodfat et al. |
| 8,090,435 B2 | 1/2012 | Gill et al. |
| 8,093,212 B2 | 1/2012 | Gardner et al. |
| 8,109,893 B2 | 2/2012 | Lande |
| 8,109,921 B2 | 2/2012 | Estes et al. |
| 8,114,350 B1 | 2/2012 | Silver et al. |
| 8,118,770 B2 | 2/2012 | Galley et al. |
| 8,119,593 B2 | 2/2012 | Richardson et al. |
| 8,123,717 B2 | 2/2012 | Weinert et al. |
| 8,127,046 B2 | 2/2012 | Grant et al. |
| 8,129,429 B2 | 3/2012 | Sporn et al. |
| 8,140,312 B2 | 3/2012 | Hayter et al. |
| 8,140,356 B2 | 3/2012 | Dicks et al. |
| 8,147,446 B2 | 4/2012 | Yodfat et al. |
| 8,147,451 B2 | 4/2012 | Brockman et al. |
| 8,152,789 B2 | 4/2012 | Starkweather et al. |
| 8,170,721 B2 | 5/2012 | Nickerson |
| 8,182,445 B2 | 5/2012 | Moubayed et al. |
| 8,182,447 B2 | 5/2012 | Moberg et al. |
| 8,192,394 B2 | 6/2012 | Estes et al. |
| 8,192,395 B2 | 6/2012 | Estes et al. |
| 8,202,267 B2 | 6/2012 | Field et al. |
| 8,204,729 B2 | 6/2012 | Sher |
| 8,206,296 B2 | 6/2012 | Jennewine |
| 8,206,350 B2 | 6/2012 | Mann et al. |
| 8,208,984 B2 | 6/2012 | Blomquist et al. |
| 8,219,222 B2 | 7/2012 | Blomquist |
| 8,221,345 B2 | 7/2012 | Blomquist |
| 8,226,891 B2 | 7/2012 | Sloan et al. |
| 8,231,562 B2 | 7/2012 | Buck et al. |
| 8,231,578 B2 | 7/2012 | Fathallah et al. |
| 8,234,126 B1 | 7/2012 | Estes |
| 8,234,128 B2 | 7/2012 | Martucci et al. |
| 8,236,242 B2 | 8/2012 | Drucker et al. |
| 8,237,715 B2 | 8/2012 | Buck et al. |
| 8,246,540 B2 | 8/2012 | Ginsberg |
| 8,249,683 B2 | 8/2012 | Wang et al. |
| 8,249,894 B2 | 8/2012 | Brown |
| 8,250,483 B2 | 8/2012 | Blomquist |
| 8,251,904 B2 | 8/2012 | Zivitz et al. |
| 8,251,906 B2 | 8/2012 | Brauker et al. |
| 8,257,259 B2 | 9/2012 | Brauker et al. |
| 8,257,300 B2 | 9/2012 | Budiman et al. |
| 8,260,630 B2 | 9/2012 | Brown |
| 8,262,617 B2 | 9/2012 | Aeschlimann et al. |
| 8,267,892 B2 | 9/2012 | Spencer et al. |
| 8,267,893 B2 | 9/2012 | Moberg et al. |
| 8,275,438 B2 | 9/2012 | Simpson |
| 8,277,435 B2 | 10/2012 | Estes |
| 8,285,328 B2 | 10/2012 | Caffey et al. |
| 8,287,454 B2 | 10/2012 | Wolpert et al. |
| 8,287,495 B2 | 10/2012 | Michaud et al. |
| 8,287,514 B2 | 10/2012 | Miller et al. |
| 8,294,581 B2 | 10/2012 | Kamen |
| 8,298,184 B2 | 10/2012 | DiPerna et al. |
| 8,311,749 B2 | 11/2012 | Brauker et al. |
| 8,313,433 B2 | 11/2012 | Cohen et al. |
| 8,321,366 B2 | 11/2012 | West et al. |
| 8,328,754 B2 | 12/2012 | Estes et al. |
| 8,328,793 B2 | 12/2012 | Birkenbach et al. |
| 8,340,792 B2 | 12/2012 | Condurso et al. |
| 8,343,092 B2 | 1/2013 | Rush et al. |
| 8,344,847 B2 | 1/2013 | Moberg et al. |
| 8,346,399 B2 | 1/2013 | Blomquist |
| 8,348,885 B2 | 1/2013 | Moberg et al. |
| 8,348,886 B2 | 1/2013 | Kanderian, Jr. et al. |
| 8,348,923 B2 | 1/2013 | Kanderian, Jr. et al. |
| 8,372,040 B2 | 2/2013 | Huang et al. |
| 8,376,943 B2 | 2/2013 | Kovach et al. |

(56) References Cited

U.S. PATENT DOCUMENTS

| | | |
|---|---|---|
| 8,385,972 B2 | 2/2013 | Bochenko et al. |
| 8,401,194 B2 | 3/2013 | Nierzwick et al. |
| 8,402,151 B2 | 3/2013 | Young et al. |
| 8,414,523 B2 | 4/2013 | Blomquist et al. |
| 8,451,230 B2 | 5/2013 | Celentano et al. |
| 8,452,413 B2 | 5/2013 | Young et al. |
| 8,452,953 B2 | 5/2013 | Buck et al. |
| 8,454,510 B2 | 6/2013 | Yodfat et al. |
| 8,454,554 B2 | 6/2013 | Reinke |
| 8,454,576 B2 | 6/2013 | Mastrototaro et al. |
| 8,454,581 B2 | 6/2013 | Estes et al. |
| 8,457,901 B2 | 6/2013 | Beshan et al. |
| 8,460,231 B2 | 6/2013 | Brauker et al. |
| 8,465,460 B2 | 6/2013 | Yodfat et al. |
| 8,469,933 B2 | 6/2013 | Zhang et al. |
| 8,533,475 B2 | 9/2013 | Frikart et al. |
| 8,552,880 B2 | 10/2013 | Kopp et al. |
| 8,562,558 B2 | 10/2013 | Kamath et al. |
| 8,573,027 B2 | 11/2013 | Rosinko et al. |
| 8,579,853 B2 | 11/2013 | Reggiardo et al. |
| 8,601,465 B2 | 12/2013 | Bernstein et al. |
| 8,650,937 B2 | 2/2014 | Brown |
| 8,657,779 B2 | 2/2014 | Blomquist |
| 8,712,748 B2 | 4/2014 | Thukral et al. |
| 8,718,949 B2 | 5/2014 | Blomquist et al. |
| 8,775,877 B2 | 7/2014 | Mcvey et al. |
| 8,801,657 B2 | 8/2014 | Blomquist et al. |
| 8,882,701 B2 | 11/2014 | DeBelser et al. |
| 8,929,823 B2 | 1/2015 | Mears et al. |
| 8,938,306 B2 | 1/2015 | Lebel et al. |
| 8,986,253 B2 | 3/2015 | DiPerna |
| 9,008,803 B2 | 4/2015 | Blomquist |
| 9,037,254 B2 | 5/2015 | John |
| 9,238,100 B2 | 1/2016 | Kruse et al. |
| 9,335,910 B2 | 5/2016 | Farnan et al. |
| 9,364,679 B2 | 6/2016 | John |
| 9,381,297 B2 | 7/2016 | Brown |
| 9,486,171 B2 | 11/2016 | Saint |
| 9,492,608 B2 | 11/2016 | Saint |
| 9,669,160 B2 | 6/2017 | Harris et al. |
| 9,715,327 B2 | 7/2017 | Rosinko et al. |
| 9,814,835 B2 | 11/2017 | Kruse et al. |
| 9,833,177 B2 | 12/2017 | Blomquist |
| 9,867,937 B2 | 1/2018 | Saint et al. |
| 9,867,953 B2 | 1/2018 | Rosinko |
| 9,980,140 B1 | 5/2018 | Spencer et al. |
| 10,016,561 B2 | 7/2018 | Saint et al. |
| 10,052,049 B2 | 8/2018 | Blomquist et al. |
| 10,213,547 B2 | 2/2019 | Rosinko |
| 10,357,606 B2 | 7/2019 | Rosinko et al. |
| 10,357,607 B2 | 7/2019 | Blomquist et al. |
| 10,549,051 B2 | 2/2020 | Rosinko |
| 10,569,016 B2 | 2/2020 | Rosinko |
| 10,653,834 B2 | 5/2020 | Kruse et al. |
| 10,864,322 B2 | 12/2020 | Saint et al. |
| 10,943,687 B2 | 3/2021 | Blomquist |
| 2001/0001144 A1 | 5/2001 | Kapp |
| 2001/0031944 A1 | 10/2001 | Peterson et al. |
| 2001/0037217 A1 | 11/2001 | Abensour et al. |
| 2001/0041831 A1 | 11/2001 | Starkweather et al. |
| 2002/0002326 A1 | 1/2002 | Causey, III et al. |
| 2002/0016568 A1 | 2/2002 | Lebel et al. |
| 2002/0019606 A1 | 2/2002 | Lebel et al. |
| 2002/0040208 A1 | 4/2002 | Flaherty et al. |
| 2002/0065454 A1 | 5/2002 | Lebel et al. |
| 2002/0072733 A1 | 6/2002 | Flaherty |
| 2002/0072932 A1 | 6/2002 | Swamy |
| 2002/0076679 A1 | 6/2002 | Aman |
| 2002/0077852 A1 | 6/2002 | Ford et al. |
| 2002/0107476 A1 | 8/2002 | Mann et al. |
| 2002/0117214 A1 | 8/2002 | Tucker et al. |
| 2002/0126036 A1 | 9/2002 | Flaherty |
| 2002/0143290 A1 | 10/2002 | Bui |
| 2002/0143580 A1 | 10/2002 | Bristol et al. |
| 2002/0183693 A1 | 12/2002 | Peterson et al. |
| 2002/0193679 A1 | 12/2002 | Malave et al. |
| 2003/0032867 A1 | 2/2003 | Crothall et al. |
| 2003/0036683 A1 | 2/2003 | Kehr et al. |
| 2003/0050621 A1 | 3/2003 | Lebel et al. |
| 2003/0055380 A1 | 3/2003 | Flaherty |
| 2003/0060765 A1 | 3/2003 | Campbell et al. |
| 2003/0065308 A1 | 4/2003 | Lebel et al. |
| 2003/0088238 A1 | 5/2003 | Poulsen et al. |
| 2003/0104982 A1 | 6/2003 | Wittmann et al. |
| 2003/0114836 A1 | 6/2003 | Estes et al. |
| 2003/0130616 A1 | 7/2003 | Steil et al. |
| 2003/0145854 A1 | 8/2003 | Hickle |
| 2003/0159945 A1 | 8/2003 | Miyazaki et al. |
| 2003/0160683 A1 | 8/2003 | Blomquist |
| 2003/0161744 A1 | 8/2003 | Vilks et al. |
| 2003/0163088 A1 | 8/2003 | Blomquist |
| 2003/0163090 A1 | 8/2003 | Blomquist et al. |
| 2003/0163223 A1 | 8/2003 | Blomquist |
| 2003/0163789 A1 | 8/2003 | Blomquist |
| 2003/0199854 A1 | 10/2003 | Kovach et al. |
| 2003/0208113 A1 | 11/2003 | Mault et al. |
| 2003/0212364 A1 | 11/2003 | Mann et al. |
| 2003/0212379 A1 | 11/2003 | Bylund et al. |
| 2003/0236489 A1 | 12/2003 | Jacobson et al. |
| 2004/0010207 A1 | 1/2004 | Flaherty et al. |
| 2004/0015102 A1 | 1/2004 | Cummings et al. |
| 2004/0015132 A1 | 1/2004 | Brown |
| 2004/0054263 A1 | 3/2004 | Moerman et al. |
| 2004/0068230 A1 | 4/2004 | Estes et al. |
| 2004/0073095 A1 | 4/2004 | Causey, III et al. |
| 2004/0078028 A1 | 4/2004 | Flaherty et al. |
| 2004/0092865 A1 | 5/2004 | Flaherty et al. |
| 2004/0100507 A1 | 5/2004 | Hayner et al. |
| 2004/0115067 A1 | 6/2004 | Rush et al. |
| 2004/0116866 A1 | 6/2004 | Gorman et al. |
| 2004/0122353 A1 | 6/2004 | Shahmirian et al. |
| 2004/0152622 A1 | 8/2004 | Keith et al. |
| 2004/0180810 A1 | 9/2004 | Pilarski |
| 2004/0193025 A1 | 9/2004 | Steil et al. |
| 2004/0193090 A1 | 9/2004 | Lebel et al. |
| 2004/0204673 A1 | 10/2004 | Flaherty |
| 2004/0220551 A1 | 11/2004 | Flaherty et al. |
| 2004/0225252 A1 | 11/2004 | Gillespie et al. |
| 2004/0235446 A1 | 11/2004 | Flaherty et al. |
| 2004/0254434 A1 | 12/2004 | Goodnow et al. |
| 2004/0260233 A1 | 12/2004 | Garibotto et al. |
| 2005/0021006 A1 | 1/2005 | Tonnies |
| 2005/0022274 A1 | 1/2005 | Campbell et al. |
| 2005/0027182 A1 | 2/2005 | Siddiqui et al. |
| 2005/0030164 A1 | 2/2005 | Blomquist |
| 2005/0049179 A1 | 3/2005 | Davidson et al. |
| 2005/0050621 A1 | 3/2005 | Thomas |
| 2005/0065464 A1 | 3/2005 | Talbot et al. |
| 2005/0065760 A1 | 3/2005 | Murtfeldt et al. |
| 2005/0081847 A1 | 4/2005 | Lee et al. |
| 2005/0095063 A1 | 5/2005 | Fathallah et al. |
| 2005/0137530 A1 | 6/2005 | Campbell et al. |
| 2005/0143864 A1 | 6/2005 | Blomquist |
| 2005/0171512 A1 | 8/2005 | Flaherty |
| 2005/0171513 A1 | 8/2005 | Mann et al. |
| 2005/0177135 A1 | 8/2005 | Hildebrand |
| 2005/0182358 A1 | 8/2005 | Veit et al. |
| 2005/0192557 A1 | 9/2005 | Brauker et al. |
| 2005/0197553 A1 | 9/2005 | Cooper |
| 2005/0197621 A1 | 9/2005 | Poulsen et al. |
| 2005/0203349 A1 | 9/2005 | Nanikashvili |
| 2005/0203360 A1 | 9/2005 | Brauker et al. |
| 2005/0228234 A1 | 10/2005 | Yang |
| 2005/0238507 A1 | 10/2005 | Diianni et al. |
| 2005/0272640 A1 | 12/2005 | Doyle, III et al. |
| 2005/0277872 A1 | 12/2005 | Colby, Jr. et al. |
| 2005/0277912 A1 | 12/2005 | John |
| 2006/0001538 A1 | 1/2006 | Kraft et al. |
| 2006/0001550 A1 | 1/2006 | Mann et al. |
| 2006/0014670 A1 | 1/2006 | Green et al. |
| 2006/0031094 A1 | 2/2006 | Cohen et al. |
| 2006/0041229 A1 | 2/2006 | Garibotto et al. |
| 2006/0047192 A1 | 3/2006 | Hellwig et al. |
| 2006/0047538 A1 | 3/2006 | Condurso et al. |

(56) References Cited

U.S. PATENT DOCUMENTS

| | | |
|---|---|---|
| 2006/0080059 A1 | 4/2006 | Stupp et al. |
| 2006/0085223 A1 | 4/2006 | Anderson et al. |
| 2006/0094985 A1 | 5/2006 | Aceti et al. |
| 2006/0122577 A1 | 6/2006 | Poulsen et al. |
| 2006/0132292 A1 | 6/2006 | Blomquist |
| 2006/0137695 A1 | 6/2006 | Hellwig et al. |
| 2006/0167345 A1 | 7/2006 | Vespasiani |
| 2006/0173406 A1 | 8/2006 | Hayes et al. |
| 2006/0173444 A1 | 8/2006 | Choy et al. |
| 2006/0178633 A1 | 8/2006 | Garibotto et al. |
| 2006/0184154 A1 | 8/2006 | Moberg et al. |
| 2006/0202859 A1 | 9/2006 | Mastrototaro et al. |
| 2006/0224109 A1 | 10/2006 | Steil et al. |
| 2006/0253097 A1 | 11/2006 | Braig et al. |
| 2006/0264895 A1 | 11/2006 | Flanders |
| 2006/0271020 A1 | 11/2006 | Huang et al. |
| 2006/0272652 A1 | 12/2006 | Stocker et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0016449 A1 | 1/2007 | Cohen et al. |
| 2007/0021733 A1 | 1/2007 | Hansen et al. |
| 2007/0033074 A1 | 2/2007 | Nitzan et al. |
| 2007/0060796 A1 | 3/2007 | Kim |
| 2007/0060871 A1 | 3/2007 | Istoc et al. |
| 2007/0060874 A1 | 3/2007 | Nesbitt et al. |
| 2007/0066956 A1 | 3/2007 | Finkel |
| 2007/0083152 A1 | 4/2007 | Williams et al. |
| 2007/0083335 A1 | 4/2007 | Moerman |
| 2007/0093786 A1 | 4/2007 | Goldsmith et al. |
| 2007/0100222 A1 | 5/2007 | Mastrototaro et al. |
| 2007/0106135 A1 | 5/2007 | Sloan et al. |
| 2007/0112298 A1 | 5/2007 | Mueller, Jr. et al. |
| 2007/0112299 A1 | 5/2007 | Smit et al. |
| 2007/0118405 A1 | 5/2007 | Campbell et al. |
| 2007/0124002 A1 | 5/2007 | Estes et al. |
| 2007/0149861 A1 | 6/2007 | Crothall et al. |
| 2007/0149926 A1 | 6/2007 | Moberg et al. |
| 2007/0156033 A1 | 7/2007 | Causey, III et al. |
| 2007/0156457 A1 | 7/2007 | Brown |
| 2007/0173712 A1 | 7/2007 | Shah et al. |
| 2007/0179355 A1 | 8/2007 | Rosen |
| 2007/0203454 A1 | 8/2007 | Shermer et al. |
| 2007/0213657 A1 | 9/2007 | Jennewine et al. |
| 2007/0233051 A1 | 10/2007 | Hohl et al. |
| 2007/0251835 A1 | 11/2007 | Mehta et al. |
| 2007/0253021 A1 | 11/2007 | Mehta et al. |
| 2007/0253380 A1 | 11/2007 | Jollota et al. |
| 2007/0254593 A1 | 11/2007 | Jollota et al. |
| 2007/0255116 A1 | 11/2007 | Mehta et al. |
| 2007/0255125 A1 | 11/2007 | Moberg et al. |
| 2007/0255126 A1 | 11/2007 | Moberg et al. |
| 2007/0255250 A1 | 11/2007 | Moberg et al. |
| 2007/0255348 A1 | 11/2007 | Holtzclaw |
| 2007/0258395 A1 | 11/2007 | Jollota et al. |
| 2007/0287985 A1 | 12/2007 | Estes et al. |
| 2007/0299389 A1 | 12/2007 | Halbert et al. |
| 2008/0004601 A1 | 1/2008 | Jennewine et al. |
| 2008/0030369 A1 | 2/2008 | Mann et al. |
| 2008/0033357 A1 | 2/2008 | Mann et al. |
| 2008/0033360 A1 | 2/2008 | Evans et al. |
| 2008/0033361 A1 | 2/2008 | Evans et al. |
| 2008/0051709 A1 | 2/2008 | Mounce et al. |
| 2008/0051714 A1 | 2/2008 | Moberg et al. |
| 2008/0051716 A1 | 2/2008 | Stutz |
| 2008/0058773 A1 | 3/2008 | John |
| 2008/0065007 A1 | 3/2008 | Peterson et al. |
| 2008/0065016 A1 | 3/2008 | Peterson et al. |
| 2008/0071209 A1 | 3/2008 | Moubayed et al. |
| 2008/0071210 A1 | 3/2008 | Moubayed et al. |
| 2008/0071217 A1 | 3/2008 | Moubayed et al. |
| 2008/0071251 A1 | 3/2008 | Moubayed et al. |
| 2008/0071580 A1 | 3/2008 | Marcus et al. |
| 2008/0076969 A1 | 3/2008 | Kraft et al. |
| 2008/0082363 A1 | 4/2008 | Habashi |
| 2008/0097289 A1 | 4/2008 | Steil et al. |
| 2008/0106431 A1 | 5/2008 | Blomquist |
| 2008/0114299 A1 | 5/2008 | Damgaard-Sorensen et al. |
| 2008/0119705 A1 | 5/2008 | Patel et al. |
| 2008/0132844 A1 | 6/2008 | Peterson et al. |
| 2008/0139907 A1 | 6/2008 | Rao et al. |
| 2008/0147004 A1 | 6/2008 | Mann et al. |
| 2008/0147041 A1 | 6/2008 | Kristensen |
| 2008/0147042 A1 | 6/2008 | Pettis et al. |
| 2008/0147050 A1 | 6/2008 | Mann et al. |
| 2008/0154513 A1 | 6/2008 | Kovatchev et al. |
| 2008/0160492 A1 | 7/2008 | Campbell et al. |
| 2008/0171697 A1 | 7/2008 | Jacotot et al. |
| 2008/0171967 A1 | 7/2008 | Blomquist et al. |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0177165 A1 | 7/2008 | Blomquist et al. |
| 2008/0183060 A1 | 7/2008 | Steil et al. |
| 2008/0201325 A1* | 8/2008 | Doniger ............... G06N 20/00 707/999.005 |
| 2008/0206799 A1 | 8/2008 | Blomquist |
| 2008/0221523 A1 | 9/2008 | Moberg et al. |
| 2008/0222246 A1 | 9/2008 | Ebling et al. |
| 2008/0228056 A1 | 9/2008 | Blomquist et al. |
| 2008/0249470 A1 | 10/2008 | Malave et al. |
| 2008/0255438 A1 | 10/2008 | Saidara et al. |
| 2008/0255517 A1 | 10/2008 | Nair et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287922 A1 | 11/2008 | Panduro |
| 2008/0288115 A1 | 11/2008 | Rusnak et al. |
| 2008/0294024 A1 | 11/2008 | Cosentino et al. |
| 2008/0294142 A1 | 11/2008 | Patel et al. |
| 2008/0294294 A1 | 11/2008 | Blomquist |
| 2008/0300534 A1 | 12/2008 | Blomquist |
| 2008/0300572 A1 | 12/2008 | Rankers et al. |
| 2008/0306434 A1 | 12/2008 | Dobbles et al. |
| 2008/0306444 A1 | 12/2008 | Brister et al. |
| 2008/0312585 A1 | 12/2008 | Brukalo et al. |
| 2009/0005726 A1 | 1/2009 | Jones et al. |
| 2009/0006061 A1 | 1/2009 | Thukral et al. |
| 2009/0018779 A1 | 1/2009 | Cohen et al. |
| 2009/0030733 A1 | 1/2009 | Cohen et al. |
| 2009/0036753 A1 | 2/2009 | King |
| 2009/0037020 A1 | 2/2009 | Brown |
| 2009/0054475 A1 | 2/2009 | Chen et al. |
| 2009/0062729 A1 | 3/2009 | Woo |
| 2009/0069745 A1 | 3/2009 | Estes et al. |
| 2009/0069749 A1 | 3/2009 | Miller et al. |
| 2009/0069784 A1 | 3/2009 | Estes et al. |
| 2009/0069787 A1 | 3/2009 | Estes et al. |
| 2009/0088731 A1 | 4/2009 | Campbell et al. |
| 2009/0093756 A1 | 4/2009 | Minaie et al. |
| 2009/0105636 A1 | 4/2009 | Hayter et al. |
| 2009/0105646 A1 | 4/2009 | Hendrixson et al. |
| 2009/0112626 A1 | 4/2009 | Talbot et al. |
| 2009/0131860 A1 | 5/2009 | Nielsen |
| 2009/0131861 A1 | 5/2009 | Braig et al. |
| 2009/0143661 A1 | 6/2009 | Taub et al. |
| 2009/0150186 A1 | 6/2009 | Cohen et al. |
| 2009/0150865 A1 | 6/2009 | Young et al. |
| 2009/0156990 A1 | 6/2009 | Wenger et al. |
| 2009/0157003 A1 | 6/2009 | Jones et al. |
| 2009/0157202 A1 | 6/2009 | Roberts et al. |
| 2009/0158274 A1 | 6/2009 | Roberts |
| 2009/0163855 A1 | 6/2009 | Shin et al. |
| 2009/0164239 A1 | 6/2009 | Hayter et al. |
| 2009/0171269 A1 | 7/2009 | Jennewine et al. |
| 2009/0177142 A1 | 7/2009 | Blomquist et al. |
| 2009/0177147 A1 | 7/2009 | Blomquist et al. |
| 2009/0177154 A1 | 7/2009 | Blomquist |
| 2009/0177180 A1 | 7/2009 | Rubalcaba, Jr. et al. |
| 2009/0192366 A1 | 7/2009 | Mensinger et al. |
| 2009/0192724 A1 | 7/2009 | Brauker et al. |

(56) References Cited

U.S. PATENT DOCUMENTS

| | | |
|---|---|---|
| 2009/0192745 A1 | 7/2009 | Kamath et al. |
| 2009/0212966 A1 | 8/2009 | Panduro |
| 2009/0216100 A1 | 8/2009 | Ebner et al. |
| 2009/0221890 A1 | 9/2009 | Saffer et al. |
| 2009/0247931 A1 | 10/2009 | Damgaard-Sorensen |
| 2009/0247982 A1 | 10/2009 | Krulevitch et al. |
| 2009/0254037 A1 | 10/2009 | Bryant, Jr. et al. |
| 2009/0256527 A1 | 10/2009 | Welsch et al. |
| 2009/0267774 A1 | 10/2009 | Enegren et al. |
| 2009/0267775 A1 | 10/2009 | Enegren et al. |
| 2009/0270705 A1 | 10/2009 | Enegren et al. |
| 2009/0275887 A1 | 11/2009 | Estes |
| 2009/0281393 A1 | 11/2009 | Smith |
| 2010/0008795 A1 | 1/2010 | DiPerna |
| 2010/0010330 A1 | 1/2010 | Rankers et al. |
| 2010/0022937 A1 | 1/2010 | Bedingfield et al. |
| 2010/0030045 A1 | 2/2010 | Gottlieb et al. |
| 2010/0030387 A1 | 2/2010 | Sen |
| 2010/0037680 A1 | 2/2010 | Moberg et al. |
| 2010/0056993 A1 | 3/2010 | Chase |
| 2010/0057043 A1 | 3/2010 | Kovatchev et al. |
| 2010/0064257 A1 | 3/2010 | Buck et al. |
| 2010/0069730 A1 | 3/2010 | Bergstrom et al. |
| 2010/0081993 A1 | 4/2010 | O'Connor |
| 2010/0094110 A1 | 4/2010 | Heller et al. |
| 2010/0095229 A1 | 4/2010 | Dixon et al. |
| 2010/0105999 A1 | 4/2010 | Dixon et al. |
| 2010/0114015 A1 | 5/2010 | Kanderian, Jr. et al. |
| 2010/0121169 A1 | 5/2010 | Petisce et al. |
| 2010/0121170 A1 | 5/2010 | Rule |
| 2010/0121415 A1 | 5/2010 | Skelton et al. |
| 2010/0125241 A1 | 5/2010 | Prud'Homme et al. |
| 2010/0130933 A1 | 5/2010 | Holland et al. |
| 2010/0138197 A1 | 6/2010 | Sher |
| 2010/0145276 A1 | 6/2010 | Yodfat et al. |
| 2010/0146300 A1 | 6/2010 | Brown |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0162786 A1 | 7/2010 | Keenan et al. |
| 2010/0168539 A1 | 7/2010 | Palerm et al. |
| 2010/0174266 A1 | 7/2010 | Estes |
| 2010/0174553 A1 | 7/2010 | Kaufman et al. |
| 2010/0179402 A1 | 7/2010 | Goode, Jr. et al. |
| 2010/0185142 A1 | 7/2010 | Kamen et al. |
| 2010/0185152 A1 | 7/2010 | Larsen et al. |
| 2010/0185175 A1 | 7/2010 | Kamen et al. |
| 2010/0198142 A1 | 8/2010 | Sloan et al. |
| 2010/0205001 A1 | 8/2010 | Knudsen et al. |
| 2010/0217192 A1 | 8/2010 | Moberg et al. |
| 2010/0217193 A1 | 8/2010 | Moberg et al. |
| 2010/0218132 A1 | 8/2010 | Soni et al. |
| 2010/0222765 A1 | 9/2010 | Blomquist et al. |
| 2010/0228186 A1 | 9/2010 | Estes et al. |
| 2010/0248706 A1 | 9/2010 | Potkonjak et al. |
| 2010/0249566 A1 | 9/2010 | Suess et al. |
| 2010/0261987 A1 | 10/2010 | Kamath et al. |
| 2010/0262078 A1 | 10/2010 | Blomquist |
| 2010/0262117 A1 | 10/2010 | Magni et al. |
| 2010/0262434 A1 | 10/2010 | Shaya |
| 2010/0274218 A1 | 10/2010 | Yodfat et al. |
| 2010/0274592 A1 | 10/2010 | Nitzan et al. |
| 2010/0274751 A1 | 10/2010 | Blomquist |
| 2010/0277119 A1 | 11/2010 | Montague et al. |
| 2010/0280442 A1 | 11/2010 | Shahmirian et al. |
| 2010/0286601 A1 | 11/2010 | Yodfat et al. |
| 2010/0286653 A1 | 11/2010 | Kubel et al. |
| 2010/0292556 A1 | 11/2010 | Golden |
| 2010/0292634 A1 | 11/2010 | Kircher, Jr. et al. |
| 2010/0295686 A1 | 11/2010 | Sloan et al. |
| 2010/0298685 A1 | 11/2010 | Hayter et al. |
| 2010/0298765 A1* | 11/2010 | Budiman ............ A61B 5/1495 604/66 |
| 2010/0305545 A1 | 12/2010 | Kanderian, Jr. et al. |
| 2010/0312085 A1 | 12/2010 | Andrews et al. |
| 2010/0324382 A1 | 12/2010 | Cantwell et al. |
| 2010/0324398 A1 | 12/2010 | Tzyy-Ping |
| 2010/0324853 A1 | 12/2010 | Wang et al. |
| 2010/0331651 A1 | 12/2010 | Groll |
| 2010/0331652 A1 | 12/2010 | Groll et al. |
| 2011/0004188 A1 | 1/2011 | Shekalim |
| 2011/0015509 A1 | 1/2011 | Peyser |
| 2011/0021898 A1 | 1/2011 | Wei et al. |
| 2011/0033833 A1 | 2/2011 | Blomquist et al. |
| 2011/0034792 A1 | 2/2011 | Williams et al. |
| 2011/0040247 A1 | 2/2011 | Mandro et al. |
| 2011/0040251 A1 | 2/2011 | Blomquist et al. |
| 2011/0046697 A1 | 2/2011 | Gerber et al. |
| 2011/0047499 A1 | 2/2011 | Mandro et al. |
| 2011/0053121 A1 | 3/2011 | Heaton |
| 2011/0054390 A1 | 3/2011 | Searle et al. |
| 2011/0054391 A1 | 3/2011 | Ward et al. |
| 2011/0056264 A1 | 3/2011 | Kaplan et al. |
| 2011/0058485 A1 | 3/2011 | Sloan |
| 2011/0060281 A1 | 3/2011 | Aeschlimann et al. |
| 2011/0071372 A1 | 3/2011 | Sloan et al. |
| 2011/0071464 A1 | 3/2011 | Palerm |
| 2011/0071765 A1 | 3/2011 | Yodfat et al. |
| 2011/0077963 A1 | 3/2011 | Knudsen et al. |
| 2011/0082439 A1 | 4/2011 | Wenger et al. |
| 2011/0087165 A1 | 4/2011 | Amborn et al. |
| 2011/0092788 A1 | 4/2011 | Long et al. |
| 2011/0093286 A1 | 4/2011 | Dicks et al. |
| 2011/0098548 A1 | 4/2011 | Budiman et al. |
| 2011/0098637 A1 | 4/2011 | Hill |
| 2011/0098638 A1 | 4/2011 | Chawla et al. |
| 2011/0098674 A1 | 4/2011 | Vicente et al. |
| 2011/0106011 A1 | 5/2011 | Cinar et al. |
| 2011/0106050 A1 | 5/2011 | Yodfat et al. |
| 2011/0112505 A1 | 5/2011 | Starkweather et al. |
| 2011/0112506 A1 | 5/2011 | Starkweather et al. |
| 2011/0118578 A1 | 5/2011 | Timmerman |
| 2011/0118699 A1 | 5/2011 | Yodfat et al. |
| 2011/0124996 A1 | 5/2011 | Reinke et al. |
| 2011/0124999 A1 | 5/2011 | Reggiardo et al. |
| 2011/0125095 A1 | 5/2011 | Lebel et al. |
| 2011/0126188 A1 | 5/2011 | Bernstein et al. |
| 2011/0130716 A1 | 6/2011 | Estes et al. |
| 2011/0130746 A1 | 6/2011 | Budiman |
| 2011/0133946 A1 | 6/2011 | Kopp et al. |
| 2011/0137239 A1 | 6/2011 | Debelser et al. |
| 2011/0144586 A1 | 6/2011 | Michaud et al. |
| 2011/0144616 A1 | 6/2011 | Michaud et al. |
| 2011/0152770 A1 | 6/2011 | DiPerna et al. |
| 2011/0152824 A1 | 6/2011 | DiPerna et al. |
| 2011/0160650 A1 | 6/2011 | Chong et al. |
| 2011/0160654 A1 | 6/2011 | Hanson et al. |
| 2011/0160666 A1 | 6/2011 | Hanson et al. |
| 2011/0163881 A1 | 7/2011 | Halff et al. |
| 2011/0166544 A1 | 7/2011 | Verhoef et al. |
| 2011/0166875 A1 | 7/2011 | Hayter et al. |
| 2011/0178461 A1 | 7/2011 | Chong et al. |
| 2011/0178462 A1 | 7/2011 | Moberg et al. |
| 2011/0178717 A1 | 7/2011 | Goodnow et al. |
| 2011/0184342 A1 | 7/2011 | Pesach et al. |
| 2011/0190701 A1 | 8/2011 | Remde et al. |
| 2011/0196213 A1 | 8/2011 | Thukral et al. |
| 2011/0202040 A1 | 8/2011 | Remde et al. |
| 2011/0205065 A1 | 8/2011 | Strachan et al. |
| 2011/0208123 A1 | 8/2011 | Gray et al. |
| 2011/0208155 A1 | 8/2011 | Palerm et al. |
| 2011/0213306 A1 | 9/2011 | Hanson et al. |
| 2011/0224522 A1 | 9/2011 | Fennell |
| 2011/0256024 A1 | 10/2011 | Cole et al. |
| 2011/0257625 A1 | 10/2011 | Jasperson et al. |
| 2011/0257895 A1 | 10/2011 | Brauker et al. |
| 2011/0266999 A1 | 11/2011 | Yodfat et al. |
| 2011/0320595 A1 | 12/2011 | Konishi et al. |
| 2012/0022452 A1 | 1/2012 | Welsch et al. |
| 2012/0029433 A1 | 2/2012 | Michaud et al. |
| 2012/0029941 A1 | 2/2012 | Malave et al. |
| 2012/0030610 A1 | 2/2012 | DiPerna et al. |
| 2012/0041415 A1 | 2/2012 | Estes et al. |
| 2012/0053522 A1 | 3/2012 | Yodfat et al. |

(56) References Cited

U.S. PATENT DOCUMENTS

| | | |
|---|---|---|
| 2012/0059353 A1 | 3/2012 | Kovatchev et al. |
| 2012/0059673 A1 | 3/2012 | Cohen et al. |
| 2012/0095315 A1 | 4/2012 | Tenbarge et al. |
| 2012/0095393 A1 | 4/2012 | Reinke |
| 2012/0096451 A1 | 4/2012 | Tenbarge |
| 2012/0109100 A1 | 5/2012 | Estes et al. |
| 2012/0123230 A1 | 5/2012 | Brown et al. |
| 2012/0163481 A1 | 6/2012 | Ebner et al. |
| 2012/0165614 A1 | 6/2012 | Strickland |
| 2012/0165728 A1 | 6/2012 | Strickland et al. |
| 2012/0184907 A1 | 7/2012 | Smith |
| 2012/0185267 A1 | 7/2012 | Kamen et al. |
| 2012/0191061 A1 | 7/2012 | Yodfat et al. |
| 2012/0191063 A1 | 7/2012 | Brauker et al. |
| 2012/0226124 A1 | 9/2012 | Blomquist |
| 2012/0232484 A1 | 9/2012 | Blomquist |
| 2012/0232485 A1 | 9/2012 | Blomquist |
| 2012/0232520 A1 | 9/2012 | Sloan et al. |
| 2012/0232521 A1 | 9/2012 | Blomquist |
| 2012/0238852 A1 | 9/2012 | Brauker et al. |
| 2012/0238854 A1 | 9/2012 | Blomquist et al. |
| 2012/0239362 A1 | 9/2012 | Blomquist |
| 2012/0245524 A1 | 9/2012 | Estes et al. |
| 2012/0265722 A1 | 10/2012 | Blomquist |
| 2012/0296269 A1 | 11/2012 | Blomquist |
| 2012/0330227 A1 | 12/2012 | Budiman et al. |
| 2013/0012917 A1 | 1/2013 | Miller et al. |
| 2013/0053816 A1 | 2/2013 | DiPERNA et al. |
| 2013/0096953 A1 | 4/2013 | Beverly et al. |
| 2013/0116649 A1 | 5/2013 | Breton et al. |
| 2013/0131630 A1 | 5/2013 | Blomquist |
| 2013/0142367 A1 | 6/2013 | Berry et al. |
| 2013/0172710 A1 | 7/2013 | Mears |
| 2013/0231711 A1 | 9/2013 | Kaib |
| 2013/0237947 A1 | 9/2013 | Amirouche |
| 2013/0283196 A1 | 10/2013 | Farnan |
| 2013/0324928 A1 | 12/2013 | Kruse |
| 2013/0331790 A1 | 12/2013 | Brown |
| 2013/0332874 A1 | 12/2013 | Rosinko et al. |
| 2013/0345625 A1 | 12/2013 | Causey, III et al. |
| 2014/0012511 A1 | 1/2014 | Mensinger et al. |
| 2014/0019396 A1 | 1/2014 | Carlsgaard et al. |
| 2014/0039392 A1 | 2/2014 | Geipel et al. |
| 2014/0066890 A1 | 3/2014 | Sloan et al. |
| 2014/0074059 A1 | 3/2014 | Howell et al. |
| 2014/0100829 A1 | 4/2014 | Mould |
| 2014/0137641 A1 | 5/2014 | Brown |
| 2014/0171772 A1 | 6/2014 | Blomquist |
| 2014/0187890 A1 | 7/2014 | Mensinger et al. |
| 2014/0273042 A1 | 9/2014 | Saint |
| 2014/0275419 A1 | 9/2014 | Ward et al. |
| 2014/0276419 A1 | 9/2014 | Rosinko et al. |
| 2014/0276420 A1 | 9/2014 | Rosinko |
| 2014/0276531 A1 | 9/2014 | Walsh |
| 2014/0276553 A1 | 9/2014 | Rosinko et al. |
| 2014/0276556 A1 | 9/2014 | Saint et al. |
| 2014/0276570 A1 | 9/2014 | Saint |
| 2014/0276574 A1 | 9/2014 | Saint |
| 2014/0350371 A1 | 11/2014 | Blomquist et al. |
| 2014/0378898 A1 | 12/2014 | Rosinko |
| 2015/0073337 A1 | 3/2015 | Saint et al. |
| 2015/0182693 A1 | 7/2015 | Rosinko |
| 2015/0182695 A1 | 7/2015 | Rosinko |
| 2015/0217044 A1 | 8/2015 | Blomquist |
| 2015/0314062 A1 | 11/2015 | Blomquist et al. |
| 2016/0030669 A1 | 2/2016 | Harris et al. |
| 2016/0082188 A1 | 3/2016 | Blomquist et al. |
| 2016/0119210 A1 | 4/2016 | Koehler et al. |
| 2016/0199571 A1 | 7/2016 | Rosinko et al. |
| 2016/0228041 A1 | 8/2016 | Heller et al. |
| 2016/0256622 A1 | 9/2016 | Day |
| 2016/0271325 A1 | 9/2016 | Farnan et al. |
| 2017/0000943 A1 | 1/2017 | Blomquist et al. |
| 2017/0056590 A1 | 3/2017 | DiPerna et al. |
| 2017/0300206 A1 | 10/2017 | Rosinko et al. |
| 2018/0021514 A1 | 1/2018 | Rosinko |
| 2018/0042559 A1 | 2/2018 | Cabrera, Jr. |
| 2018/0071454 A1 | 3/2018 | Betts |
| 2018/0092578 A1 | 4/2018 | Blomquist |
| 2018/0137938 A1 | 5/2018 | Vaddiraju |
| 2018/0193573 A1 | 7/2018 | Rosinko |
| 2019/0350501 A1 | 11/2019 | Blomquist et al. |
| 2019/0365997 A1 | 12/2019 | Harris |
| 2019/0388015 A1 | 12/2019 | Blomquist |
| 2020/0101226 A1 | 4/2020 | Saint et al. |
| 2020/0114076 A1 | 4/2020 | Ulrich et al. |
| 2020/0171249 A1 | 6/2020 | Rosinko |
| 2020/0179603 A1 | 6/2020 | Rosinko |
| 2020/0261649 A1 | 8/2020 | Michaud et al. |
| 2020/0368430 A1 | 11/2020 | Ulrich et al. |
| 2021/0001044 A1 | 1/2021 | Michaud et al. |

FOREIGN PATENT DOCUMENTS

| | | |
|---|---|---|
| DE | 4407005 C1 | 3/1995 |
| DE | 19819407 A1 | 11/1999 |
| DE | 10121317 A1 | 11/2002 |
| DE | 10352456 A1 | 7/2005 |
| EP | 1102194 A2 | 5/2001 |
| EP | 1571582 A2 | 9/2005 |
| JP | 2006034323 A | 2/2006 |
| WO | WO-0045696 A1 | 8/2000 |
| WO | WO-0074753 A1 | 12/2000 |
| WO | WO-0152727 A1 | 7/2001 |
| WO | WO-02062212 A2 | 8/2002 |
| WO | WO-03082091 A2 | 10/2003 |
| WO | WO-2004093648 A2 | 11/2004 |
| WO | WO-2005046559 A2 | 5/2005 |
| WO | WO-2006061169 A1 | 6/2006 |
| WO | WO-2006127841 A2 | 11/2006 |
| WO | WO-2007000425 A2 | 1/2007 |
| WO | WO-2007056592 A2 | 5/2007 |
| WO | WO-2007089537 A1 | 8/2007 |
| WO | WO-2007149533 A2 | 12/2007 |
| WO | WO-2008048556 A2 | 4/2008 |
| WO | WO-2008048582 A1 | 4/2008 |
| WO | WO-2008048583 A1 | 4/2008 |
| WO | WO-2008048584 A1 | 4/2008 |
| WO | WO-2008048585 A1 | 4/2008 |
| WO | WO-2008048586 A1 | 4/2008 |
| WO | WO-2008048587 A1 | 4/2008 |
| WO | WO-2008091320 A2 | 7/2008 |
| WO | WO-2008112078 A2 | 9/2008 |
| WO | WO-2008153689 A1 | 12/2008 |
| WO | WO-2008153819 A1 | 12/2008 |
| WO | WO-2009016636 A2 | 2/2009 |
| WO | WO-2009032400 A1 | 3/2009 |
| WO | WO-2009032402 A1 | 3/2009 |
| WO | WO-2009035759 A1 | 3/2009 |
| WO | WO-2009088983 A2 | 7/2009 |
| WO | WO-2009089028 A2 | 7/2009 |
| WO | WO-2009089029 A2 | 7/2009 |
| WO | WO-2010056663 A2 | 5/2010 |
| WO | WO-2011068648 A2 | 6/2011 |
| WO | WO-2013016363 A2 | 1/2013 |
| WO | WO-2013184896 A1 | 12/2013 |

OTHER PUBLICATIONS

Application and File History for U.S. Appl. No. 16/394,751, filed Apr. 25, 2019, inventors Blomquist et al.
Application and File History for U.S. Appl. No. 13/828,958, filed Mar. 14, 2013, inventors Kruse et al.
Application and File History for U.S. Appl. No. 15/808,286, filed Nov. 9, 2017, inventors Kruse et al.
Application and File History for U.S. Appl. No. 14/992,709, filed Jan. 11, 2016, inventors Kruse et al.
Bott, et al., "Impact of Smoking on the Metabolic Action of Subcutaneous Regular Insulin in Type 2 Diabetic Patients," Horm. Metab. Res., vol. 37, 2005, pp. 445-449.
Chase, et at., "The Use of Insulin Pumps With Meal Bolus Alarms in Children With Type 1 Diabetes to Improve Glycemic Control," Diabetes Carem, vol. 29, No. 5, May 2006, pp. 1012-1015.

(56) References Cited

OTHER PUBLICATIONS

"Compare Insulin Pump for Diabetes," Printed from www.diabetesnet.com/diabetes-technology/insulin-pump-models.php, Jun. 18, 2009, 4 pages.

International Preliminary Reporton Patentability for Application No. PCT/US2013/044319, dated Dec. 18, 2014, 6 pages.

International Search Report and Written Opinion for Application No. PCT/US2013/044319, dated Nov. 6, 2013, 12 pages.

Lehmann, et al., "Combining rule-based reasoning and mathematical modeling in diabetes care," Artificial Intelligence in Medicine, vol. 6, 1994, pp. 137-160.

Hildebrandt P, "Subcutaneous Absorption of Insulin in Insulin-Dependent Diavetic patients. Influence of Species Physico-Chemical properties of Insulin and Physiological factors," Danish Medical Bulletin, Aug. 1991, 10 pages.

Plougmann, et al.," DiasNet—a diabetes advisory system for communication and education via the internet," International Journal of Medical Informatics, vol. 64, 2001, pp. 319-330.

Puckett, et al., "A model for multiple subcutaneous insulin injections developed from individual diabetic patient data," vol. 269, 1995, p. E1115-E1124.

Smith Medical MD Inc., "Deltec Cozmo, Personalized Insulin Pump, Starting Guide," http://web.archive.org/web/20041207133223/http://www.cozmore.com/Library/-upload/starting.sub.—guide.sub.—032004.pdf, XP002497833, Dec. 7, 2004, pp. 1-83.

Stapel E., "Converting Between Decimals, Fractions, and Percents," Purplemath, 2006, 9 pages, Available at http://www.purplemath.com/modules/percents2.htm, 2006.

Trajanoski, et al., "Pharmacokinetic Model for the Absorption of Subcutaneously Injected Soluble Insulin and Monomeric Insulin Analogues," Biomedizinische Technik, vol. 38, No. 9. Sep. 1, 1993, pp. 224-231.

Wach, et al., "Numerical Approximation of Mathematical Model for Absorption of Subcutaneously Injected Insulin," Med & Biol. Eng & comput., vol. 33, 1995, pp. 18-23.

Walsh, et al., "Diabetes Technology-Concept 1: Super Bolus," available at Diabetes Technology—Concept 1: Super Bolus available at http://www.diabetesnet.com/diabetes.sub.—technology/super.sub.—bolus.ph-p>, Sep. 17, 2007, 3 pages.

Walsh J., et al., "Select & Test Your Correction Factor," Pumping Insulin, Fourth Edition, Chapter 13, 2006, 10 Pages.

Walsh J., et al., "Select & Test Your Basal Rates," Pumping Insulin, Fourth Edition, Chapter 11, 2006, 30 pages.

Walsh J., et al., "Select and Test Your Carb Factor," Pumping Insulin, Fourth Edition, Chapter 12, 2006, 32 pages.

Walsh J., et al., "Pumping Insulin: Everything you need for Success on a Smart insulin Pump," Torrey Pines Press, San Diego, ISBN 1-884804-86-1, 2006, 3 pages.

Wikipedia.com, "Wikipedia's definition for "basal rate"," printed from wikipedia.com on Jun. 12, 2009, 1 page.

Wilinska, et al., "Insulin Kinetics in Type-1 Diabetes: Continuous and Bolus Delivery of Rapid Acting Insulin," IEEE Transactions on Biomedical Engineering, vol. 52, No. 1, Jan. 2005, pp. 3-12.

\* cited by examiner

DEVICE AND METHOD FOR TRAINING USERS OF AMBULATORY MEDICAL DEVICES

RELATED APPLICATIONS

This application is a continuation of application Ser. No. 15/808,286 filed Nov. 9, 2017, which in turn is a continuation of application Ser. No. 14/992,709 filed Jan. 11, 2016, now U.S. Pat. No. 9,814,835 issued Nov. 14, 2017, which in turn is a continuation of application Ser. No. 13/828,958 filed Mar. 14, 2013, now U.S. Pat. No. 9,238,100 issued Jan. 19, 2016, which claims the benefit of U.S. Provisional Application No. 61/656,984 filed Jun. 7, 2012, each of which is incorporated herein in its entirety by reference.

BACKGROUND

Portable ambulatory medical devices have proved useful for treating patients with medical conditions that require continuous monitoring and/or treatment. One example of such a portable ambulatory medical device is a device that involves the delivery of fluids. There are many applications in academic, industrial, and medical fields, as well as others, that involve devices capable of accurately and controllably delivering fluids, including liquids and gases, that have a beneficial effect when administered in known and controlled quantities. This is particularly true in the medical field, where treatments for many patients include the administration of a known amount of a substance at predetermined intervals. For example, the treatment of diabetes involves just such a regimented dosage of medicaments such as insulin. In addition, diabetes is one of a few medical indications wherein the patients routinely administer the medicament to themselves by a subcutaneous modality, such as a hypodermic syringe injection or by an ambulatory infusion pump. As such, providing a patient with the means to safely, reliably, and comfortably administer required doses of medication such as, e.g., insulin, may be particularly important in order to facilitate patient compliance and accurate treatment of the condition.

Ambulatory infusion pumps have been developed for the administration of medicaments such as insulin for those diagnosed with both type I and type II diabetes. These pumps offer an alternative to multiple daily injections of insulin by an insulin syringe or an insulin pen. They also allow for continuous insulin therapy. In addition, some ambulatory infusion devices can include data collection and storage mechanisms, which allow a diabetic patient/user and/or a caregiver (e.g., doctor, health care worker, family member, and so forth) to easily monitor and adjust insulin intake. The infusion device may be powered by a rechargeable battery that requires periodic recharging.

Ambulatory medical devices may include a keypad, buttons, and/or touchscreen with a display on which symbols may be displayed and from which inputs may be received for operation of the device. A series of display screens or windows may be displayed on the touchscreen, showing alphanumeric text and symbols and providing menu screens through which the user can control operation of the device and receive information regarding the device and its operation, history, settings, interaction with the user, and the like. User interaction, such as by touching the alphanumeric text and symbols, provides user input and facilitates navigation through the menu screens and selection of the device functions.

With the advancement of medical devices and the increasing complexity of the user interfaces, some users may experience difficulty interacting with the user interface of the device, such as, for example, when entering inputs to operate the device. It is desirable to reduce the number of user errors and minimize the consequences of such errors. One difficulty users can experience, particularly when interacting with touch screen user interfaces, is the accidental touch of adjacent buttons/icons. A unique complication that may be present with respect to diabetic users for ambulatory insulin pumps is that these users may build up calluses on the tips of their fingers as a result of repeated blood glucose testing. Such calluses may be especially problematic for the operation of capacitive-based touch screen pump configurations. For example, calluses may prevent or hinder the transfer of energy that the capacitive screens use to receive input, thus preventing or hindering proper use of the touch screen to control the pump by the user.

To compensate for such difficulties in operation and provide improved user interface configurations, it is common in user interface research to observe and record the user inputs for performing a given task. One of the primary methods employed to aid this analysis is the use of external video cameras to record the user input over a period of time. The resulting data analysis can be tedious, as the analysis requires, e.g., comparison of the recorded touch sequence to an ideal task sequence. Any deviation from the expected task pathway may be noted as user error. Analysis of such deviations is then used as a design input to improve the accuracy of the human interface input.

Ambulatory infusion pumps with user interfaces implemented and incorporated therein enable the patient to administer the medicament, such as insulin, to themselves. For proper operation by a user of the device, it is important that the user be adequately trained with regard to the device operation. Some users, including patients and/or caregivers, may not be adept at operating such pumps, even if they are designed for simplicity and ease of use, and may require training to ensure proper operation of the device and efficacious treatment of their medical condition. Users, including patients and/or caregivers, may experience further complications with particular devices, such as insulin delivery systems, because each individual user responds uniquely to a given insulin dosage and rate of dosage. Such devices often require training so the patient does not over-medicate or under-medicate in myriad unique "real life" scenarios. Thus, with the rapid advancement and proliferation of such portable ambulatory medical devices, there is an associated need for increased training and clinician support.

Current trends in the delivery of health care are toward reduced patient medical support and, for operation of devices such as ambulatory medicament pumps, reduced training of users. This reduction is due in part to the overloading of health care resources such as hospitals, medical professionals, and caregivers, increasing financial limitations for access to medical care, rising healthcare costs, and a shortage of well-trained clinicians and caregivers.

In view of the discussion above, there is a need for systems and methods to more effectively train users, including patients and caregivers, for efficacious operation of ambulatory medical devices to accommodate each individual patient with unique circumstances and responses to therapy and to do so with reduced support from clinicians and others, including, e.g., representatives from the manufacturer of such ambulatory medical devices (such as field clinical support personnel, customer service representatives, certified diabetes educators (CDEs), sales representatives, etc.).

In view of the discussion above, there is also a need for systems and methods to improve the accuracy, efficiency and capability of the user interface system beyond the recording and play back analysis methods currently used in touch interface development.

SUMMARY

Disclosed herein are devices, such as ambulatory portable medical devices (e.g., ambulatory pumps for the administration of insulin and other medicaments for the treatment of diabetes), and methods of improving the interaction of such devices with users. The portable device may include control features such as buttons or switches to control pumping and other factors, and the portable device may include a touch screen on which are displayed alphanumeric text, symbols, menu screens, data, alerts and other information. While in operation, the device provides features such that it receives user input and detects device parameter values at the time of the user input. The device writes the received user input and the device parameter values into memory of the device. The features may be provided in an operating mode of the device, or the features may be provided as a function or application within an operating mode of the device.

For example, the device may have one or more modes of operation including a training simulation mode, a normal operating mode, and an initial operating mode. The device may include a processor and system bus, and may also connect compatible external sensors to the system bus for gathering and storing device parameter data. In one embodiment, a normal operating mode of the device detects user interactions and records the interactions along with various device parameters at the time of the interaction, and allows a clinician to review the user's performance for the initial use period. Automated analysis software may operate to analyze the data generated by the user during the normal operating mode. The results of the analysis may be used by the clinician to improve the user and device interaction. This can be done by changing settings in the device, and/or providing additional training to the user.

Other features and advantages of the present invention should be apparent from the following description of preferred embodiments that illustrate, by way of example, the principles of the invention.

The drawings illustrate embodiments of the technology and are not limiting. For clarity and ease of illustration, the drawings may not be made to scale and, in some instances, various aspects may be shown exaggerated or enlarged to facilitate an understanding of particular embodiments.

DETAILED DESCRIPTION

Disclosed herein are embodiments directed to a portable medical device having an interactive display screen, such as a touchscreen, for control by the user, and having a connecting tube with an infusion port for administering medication to a patient.

Figure 1:
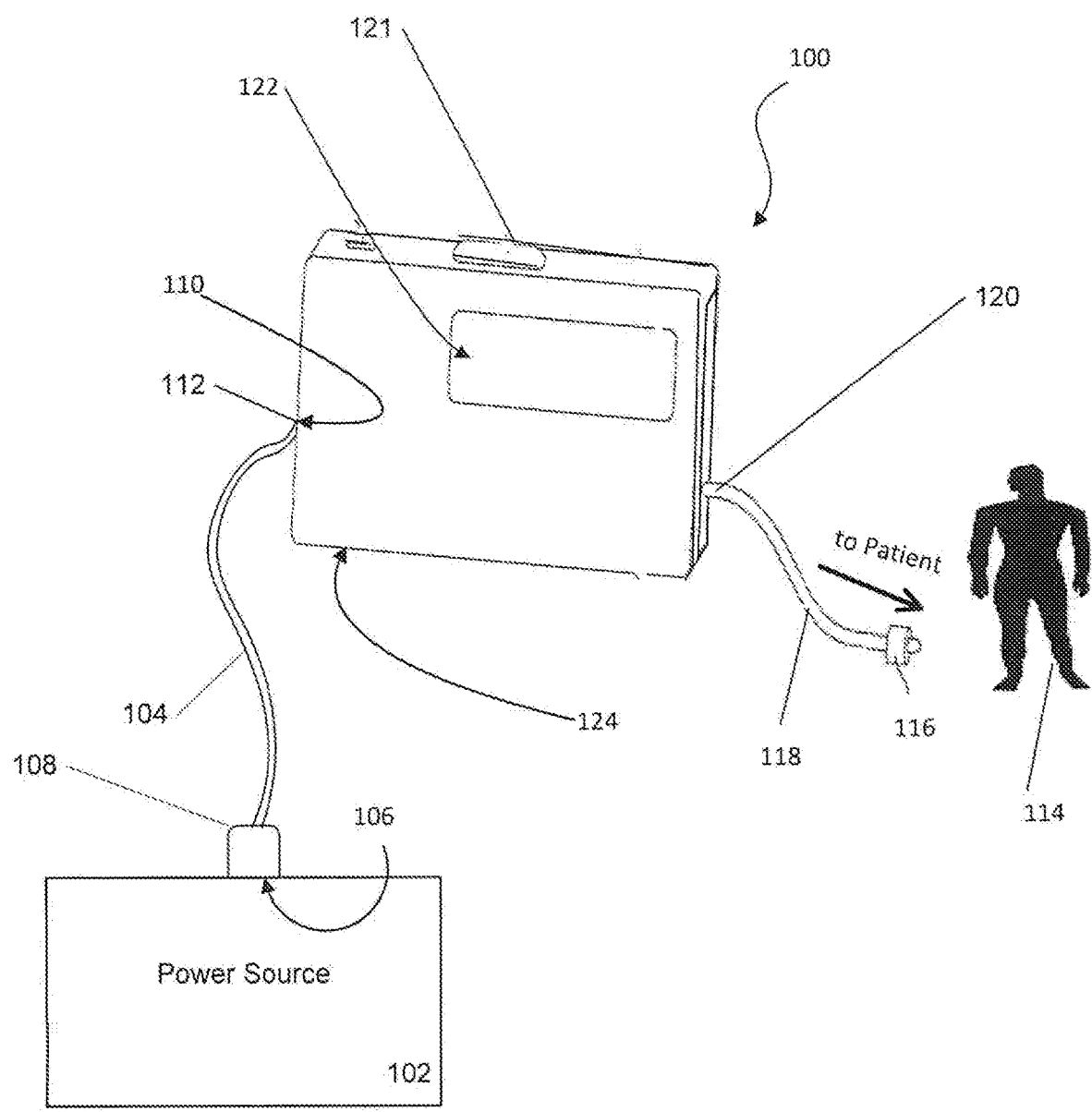
FIG. 1 depicts a portable device according to an embodiment of the present invention that is coupled to a patient for infusing medication thereto.

FIG. 1 depicts an electrically-powered portable device 100 that is coupled to a host power source 102, such as a desktop or laptop computer, through a cable 104. The cable may comprise, for example, a coupling through which both data and electrical energy are received at the portable device 100. Examples of such combined power and data cables include a Universal Serial Bus (USB) connection, an IEEE 1499 connection, a "THUNDERBOLT" connection (i.e., from Apple, Inc., of Cupertino, Calif., USA), PCI Express, eSATA and Ethernet. The host power source 102 is a source of electrical energy and the host computing device can be any type of computing device that includes a port 106 that receives a connector 108 of the cable 104. The port of the host computing device may comprise, for example, a USB port, or IEEE 1499 port, or port for THUNDERBOLT, PCI Express, eSATA and Ethernet. A compatible connector port 110 of the portable device 100 is coupled to the cable 104 at an opposite end 112 of the cable. In a USB implementation, for example, the cable 104 is a USB 5 cable and associated connections and ports may support one or more of USB version 1.1, 2.0, or 3.0 data transfer speeds.

The portable device 100 may be coupled to a patient 114 via an infusion port 116 and a connecting tube or cannula 118. The connecting tube is coupled to the portable device 100 at a fluid dispensing port 120. The portable device may include control features, such as buttons or switches 121 to receive user input and control pumping and other functions, and may include a display screen 122 on which messages and alerts are displayed. The display 122 may comprise, for example, a touchscreen on which user inputs may be received. A housing 124 of the portable device encloses internal components, such as fluid reservoirs, electrical components, battery, and the like. The portable device 100 illustrated in FIG. 1 comprises a portable medical device of the type worn by a patient 114 such that fluid such as insulin is delivered via the connecting tube 118 and the fluid dispensing port 120. Exemplary ambulatory medical devices and features include those, e.g., disclosed in U.S. patent application Ser. No. 13/557,163, U.S. patent application Ser. No. 12/714,299, U.S. patent application Ser. No. 12/538,018, U.S. Provisional Patent Application No. 61/655,883, U.S. Provisional Patent Application No. 61/656,967 and U.S. Pat. No. 8,287,495. Each of the aforementioned documents is hereby incorporated herein by reference in its entirety.

The portable device 100 can be coupled to a host power source such as a desktop or laptop computer, through a cable connected to the connector port 110. The cable may comprise, for example, a coupling through which both data and electrical energy are received at the portable device 100. Examples of such combined power and data cables include a Universal Serial Bus (USB) connection, an IEEE 1499

(FireWire) connection, a "THUNDERBOLT" connection (from Apple, Inc. of Cupertino, Calif., USA), PCI Express, eSATA and Ethernet.

The device 100 may also include a capability to operatively couple to one or more other devices via a wired or wireless (e.g., infrared, electronic, optical, etc.) link, locally or via a network, such as, e.g., a portable or non-portable medical device, a control unit, external monitor or display, a personal, laptop, tablet or mainframe computer, or mobile communication device such as a smartphone or personal digital assistant (PDA). Such other devices may control or be controlled by device 100 and/or may otherwise communicate for the transfer of data including device parameters between or among device 100 and other device(s) for analysis of data (e.g., user data for physician review, device diagnostic data for troubleshooting or repair), programming, or other uses.

The portable device 100 may include control features such as buttons, panels, screens, and/or switches to control pumping and other functions, or any combination of such control features. For example, the portable device 100 illustrated in FIG. 1 shows a touchscreen 122 on which can be displayed alphanumeric text, symbols, menu screens, data, alerts and other information for receiving control input. The portable device may include a processor with memory, wherein the processor executes program instructions to provide an operating system that supports programs that execute and provide the specified features. The touchscreen 122 may be interactive, wherein user input may be received such as by pressing the outer surface of the touchscreen. The touchscreen 122 may be configured to display menu screens or pages that allow the user to input data fields to, e.g., select device parameters, so as to allow the program to produce a suggested delivery amount, rate, profile, and/or the like in an intuitive, manipulatable, and/or graphic representation. The user can therefore interact with the screen to shape the characteristic/form of the delivery amount, rate, and/or graphic delivery profile, e.g., by manipulating the delivery estimate or pattern displayed on the screen to effectuate the actual delivery.

Figure 6:
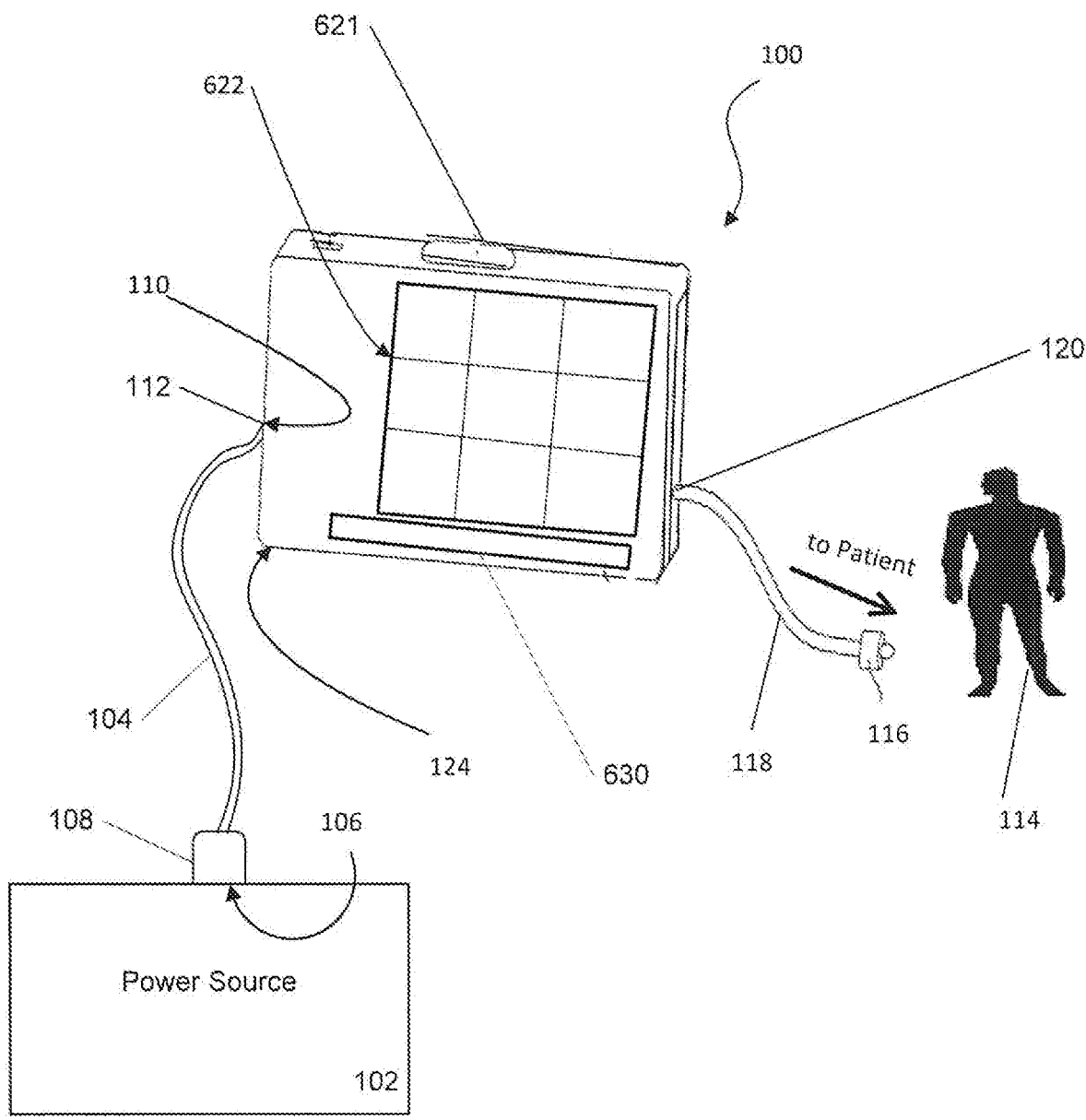
FIG. 6 depicts a keyboard-equipped portable device that is coupled to a patient for infusing medication thereto.

FIG. 6 depicts an embodiment of a portable device 600 that is coupled to a host power source 102, such as a desktop or laptop computer, through a cable 104, and is similar in construction to the embodiment illustrated in FIG. 1, except that the FIG. 6 device 600 has control features that are physical buttons, including a power switch 621 and a keypad 622 that the user presses to control the device, including actions such as pumping and the like. The device 600 includes a display 630 on which indications are displayed. Structures in FIG. 6 with like reference numerals to those in FIG. 1 relate to like structures.

Device parameters provided by the portable infusion device may be presented on the display screen 122 as any number of objects, including one or more numeric and/or alphanumeric values, a range, a value or range that is presented in the form of a drop-down menu, a toggle that can be adjusted by the user, a graphical representation (e.g., icon) or an animated graphic. For instance, in certain embodiments, the value is a range of values that are presented on a screen of the display as a toggle, wherein the toggle may be adjusted upwards or downwards by the user swiping a finger over the screen to select the appropriate value range, e.g. appropriate range of amounts of medicament such as insulin to be delivered and/or the appropriate rate, time, or interval of medicament delivery. In certain instances, the values presented in the range may be adjusted by the processor (illustrated in FIG. 2). Other device parameters will be readily apparent to those skilled in the art.

If the device includes a touchscreen 122 as in FIG. 1, the type of touchscreen may be selected as desired to be useful for a particular application, such as touchscreens comprising LCD displays, LED displays, plasma displays, organic LED (OLED) displays, and the like. The touchscreen 122 may be implemented with a capacitance screen, a resistive screen, or other such display/input technology. The portable device 100 may additionally include a keyboard or other input device known in the art for data entry, which may be separate from the display.

Figure 2:
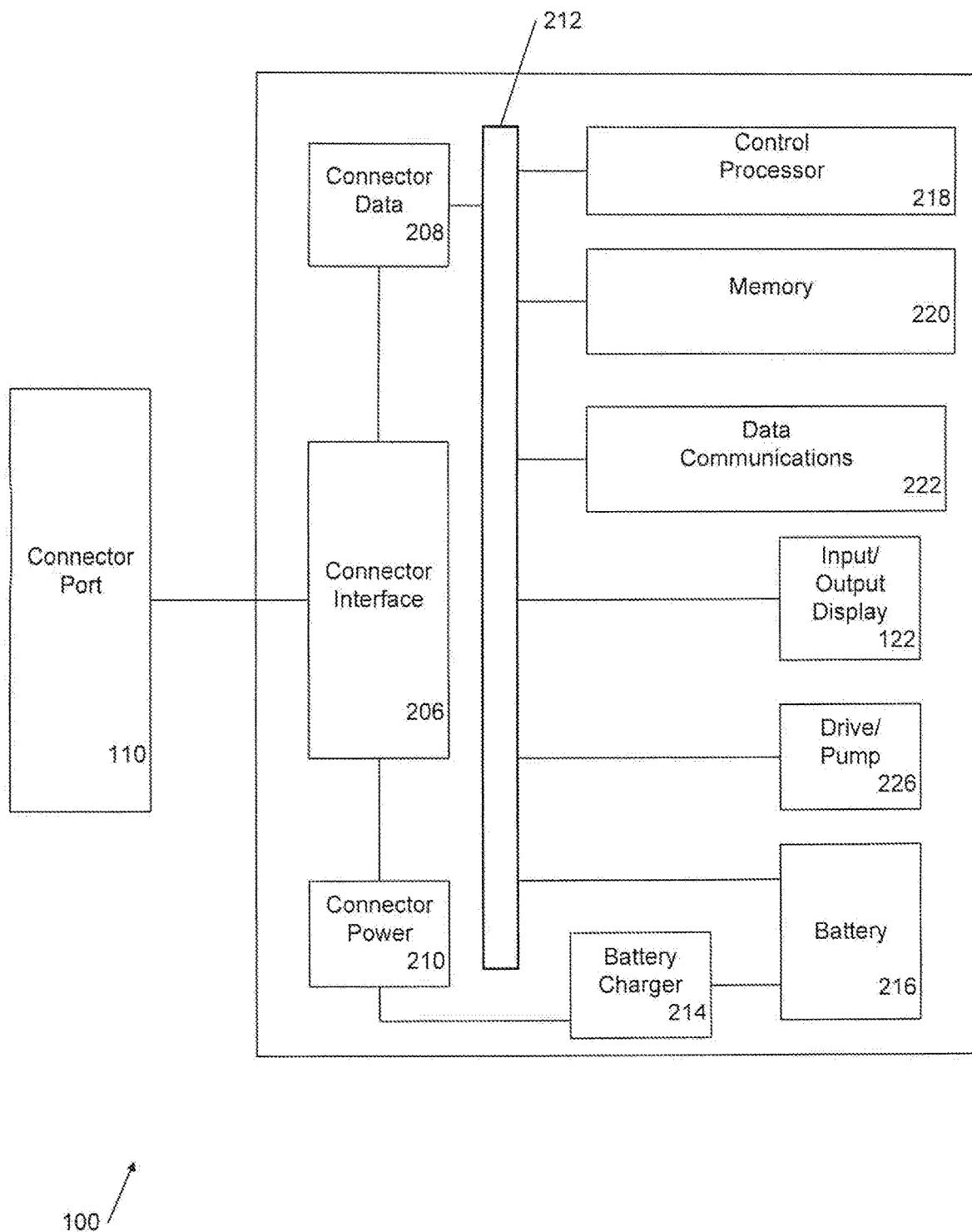
FIG. 2 is a block diagram of circuitry and components for the portable medical device of FIG. 1.

FIG. 2 depicts a block diagram of some of the components within the portable device 100 of FIG. 1. The portable device 100 includes a power management system 202 that is connected to the connector port 110 that receives a combined data/power cable, such as the USB cable 104 illustrated in FIG. 1. That is, the cable 104 has the capability of simultaneously providing electrical energy for charging and data transmission for communications. A connector interface 206 supports data exchange and receives electrical power through the connector port 110, and controls a connector data element 208 and a connector power element 210. The device may be powered by battery power in place of or in addition to the connector interface. The connector interface 206 passes data communications from the connector port 110 through the connector data element 208 to a system bus 212. The connector interface 206 passes electrical power from the connector port 110 through the connector power element 210 to a battery charger 214, which in turn is coupled to a battery 216 and which recharges the battery. In one embodiment, the connector data element 208 is implemented in the FIG. 2 device with a USB Isolation Chip ADUM4160 product from Analog Devices, Inc. of Norwood, Mass., USA, and the connector power element 210 is implemented in the FIG. 2 device with a USB Power Isolation Chip LT3573 product from Linear Technology Corporation of Milpitas, Calif., USA. Those skilled in the art will be aware of alternative suitable devices.

A control processor 218 is connected to the system bus 212 and receives the data communications from the connector data element 208 for processing. The control processor controls operation of the various elements of the portable device 100 that are connected to the system bus. The control processor operates according to mode instructions that may be stored in device memory 220.

During operation of the device according to typical usage, such as when the device provides the actions for which it is designed, the device provides features such that it receives user input and detects device parameter values at the time of the user input and writes the received user input and the device parameter values into memory of the device. In the case of a portable infusion pump, for example, the operational actions include pumping medicaments such as insulin to a patient. The parameter detecting and memory writing features of the device may be provided in an operating mode of the device, or they may be provided as a function or application within an operating mode of the device. The phrases "mode" and "function" may be used interchangeably, as required by context, as will be known to those skilled in the art.

The devices of FIG. 1 and FIG. 6 may each have one or more modes of operation. That is, each device may be capable of operating in one mode exclusively or in one or more modes simultaneously. The parameter detecting and memory writing features of the device, however, are provided in conjunction with a mode or function of the device in which the device provides the actions for which it is designed. For example, the parameter detecting and memory writing features may be provided in an operating mode of the device, such as a normal operating mode, or may be provided in a function, such as a recording function, of a single or of multiple modes.

For example, the device may have a normal operating mode where the device is attached to the patient and the device is capable of receiving and responding to user interaction, and delivering medicament as required. The device may also have a training mode in which the device may or may not be coupled to the patient and the clinician can simulate scenarios on the device while monitoring the patient's interactions with the device. The parameter detecting and memory writing features of the device as described herein would not ordinarily be available in the training mode, absent a function that permits the device to operate so as to provide the actions (e.g., pumping) for which it is designed.

The parameter detecting and memory writing features may be provided autonomously by the device, without input from the user, or providing the parameter detecting and memory writing features may require specific input from the user. In the case of specific input from the user, the parameter detecting and memory writing features may be provided as a function of the normal operating mode, initiated through a special configuration by an authorized clinician or other suitable person and comprising a temporary modification to the normal operating mode. Alternatively, the parameter detecting and memory writing features can be initiated from the time of initial power-on of the device, and continuing on for a predetermined subsequent time, at which time the parameter detecting and memory writing features are terminated. Alternatively, the device may continually monitor patient performance, without termination of the parameter detecting and memory writing features, providing a mode of operation that facilitates review of user performance at the time of a call to customer service or other request for assistance. The device may also have a playback function, wherein a user, caregiver, clinician, or the like can review data stored in the device memory.

Program instructions may be stored in processor memory incorporated in the control processor 218. The control processor also stores data including device parameters, from its operations in the device memory 220. The control processor 218 controls a data communications element 222 that may comprise a receiver/transmitter for wireless RF communications, such as "WiFi" communications or "Bluetooth" communications between the portable device 100 and compatible external systems and networks. The communications may take place over proprietary networks or links, or may take place using secure links over public networks. The device 100 includes an output/display element 122 such as a touchscreen display, operating buttons or switches. The device 100 of FIG. 1 comprises an infusion pump device, and therefore also includes a drive/pump element 226 such as a pumping mechanism for delivery of fluid such as insulin to the connecting tube 118, as described above in connection with FIG. 1. To meet industry standards and governmental regulations, the connector data element 208 and the connector power element 210 are both electrically isolated from the other device components, so as to provide a device that can be safely connected to the power source and the patient at the same time.

The device may also connect compatible external sensors to the system bus 212 for gathering and storing device parameter data. The device parameter data can be used as an input to the processor to make automated decisions, it can be reported to the user through the touchscreen 122 to aid the user in making self-medicating decisions, or it can be recorded into memory 220 for later analysis. The data may also be sent to a third party or another device for monitoring the patient's status. Other uses of such data are well known and are readily apparent to those skilled in the art. The external sensors can be any type of sensors useful for the operation of the device, such as optical, electrical, mechanical, electro-mechanical and chemical. The external sensors may be, e.g., traditional physical sensors that monitor body temperature, blood pressure, and the like, or they can be sensors that utilize chemical or biological reactions. Chemical and biological sensors differ from physical sensors, which are limited to the measurement of basic physical parameters. An exemplary and well-known chemical or biosensor is an enzyme electrode for the detection of glucose. These sensors are typically comprised of a bioactive surface consisting of immobilized glucose oxidase sandwiched between a polycarbonate and cellulose acetate membrane. The transducer is a platinum electrode and the output is typically a low current on the order of microamperes. Myriad chemical and biological sensors are available and are well known in the art such as Ph sensors for in vivo blood gasses, fiber-optic glucose sensors, biosensors based on transition metal hexcyanoferrates and chemically prepared grapheme-based nanomaterials.

The memory 220 of the device 100 may be any type of memory capable of storing data and retrieving that data for transfer to one or more other components of the device, such as the control processor 218. The memory may comprise one or more of a Flash memory, SRAM, ROM, DRAM, RAM, EPROM and dynamic storage. For the illustrated portable fluid delivery device 100 of FIG. 1, the device memory 220 may be coupled to the control processor 218 and may be configured to receive and store one or more device parameters comprising, e.g., user input data from the touchscreen, user input from buttons or switches, time, date, external sensor readings, device operating status, device messages to the user, user templates or predetermined fluid delivery patterns. The device parameters may be stored as a discrete data set at a particular point in time, a multitude of sequential discrete data sets separated by a period of time, or what is effectively termed "real-time" or continuous recording of the device parameters as fast as the system will allow. Other methods of recording device parameters such as initiating a recording based upon a trigger event are readily apparent and well known to those of skill in the art.

The memory can also be configured to store one or more personalized (e.g., user defined) delivery profiles, such as a profile based on a user's selection and/or grouping of various input parameters; past generated delivery profiles; recommended delivery profiles and one or more traditional delivery profiles, e.g., square wave, dual square wave, basal and bolus rate profiles. The memory can also store other device parameters such as user information, history of use, glucose measurements including blood glucose data and continuous glucose monitoring data, compliance and a calendar of events. An infusion workflow, or protocol, may be at least part of a program that displays a sequence of menu pages to assist a user to at least program or control the portable infusion device and/or at least one operation comprising input, change, confirm, or view various information within the device. Any part of a workflow or protocol may include any number of queries for prompting the user to enter, modify, or confirm information, which are typically presented to the user on the touchscreen display. In some embodiments, the memory 220 of the portable medical device 100 may have a data capacity of up to about 10 GB, more specifically, up to about 3 GB, even more specifically, about 1 MB to about 200 MB. In some embodiments, the memory of the infusion device 200 may be up to about 3 GB, more specifically, up to about 500 MB or more, and even more specifically, about 200 kB to about 200 MB. Larger memory sizes will permit more extensive use and operating modes, such as continual use in recording device parameters and/or user interactions, rather than initial use.

Figure 3:
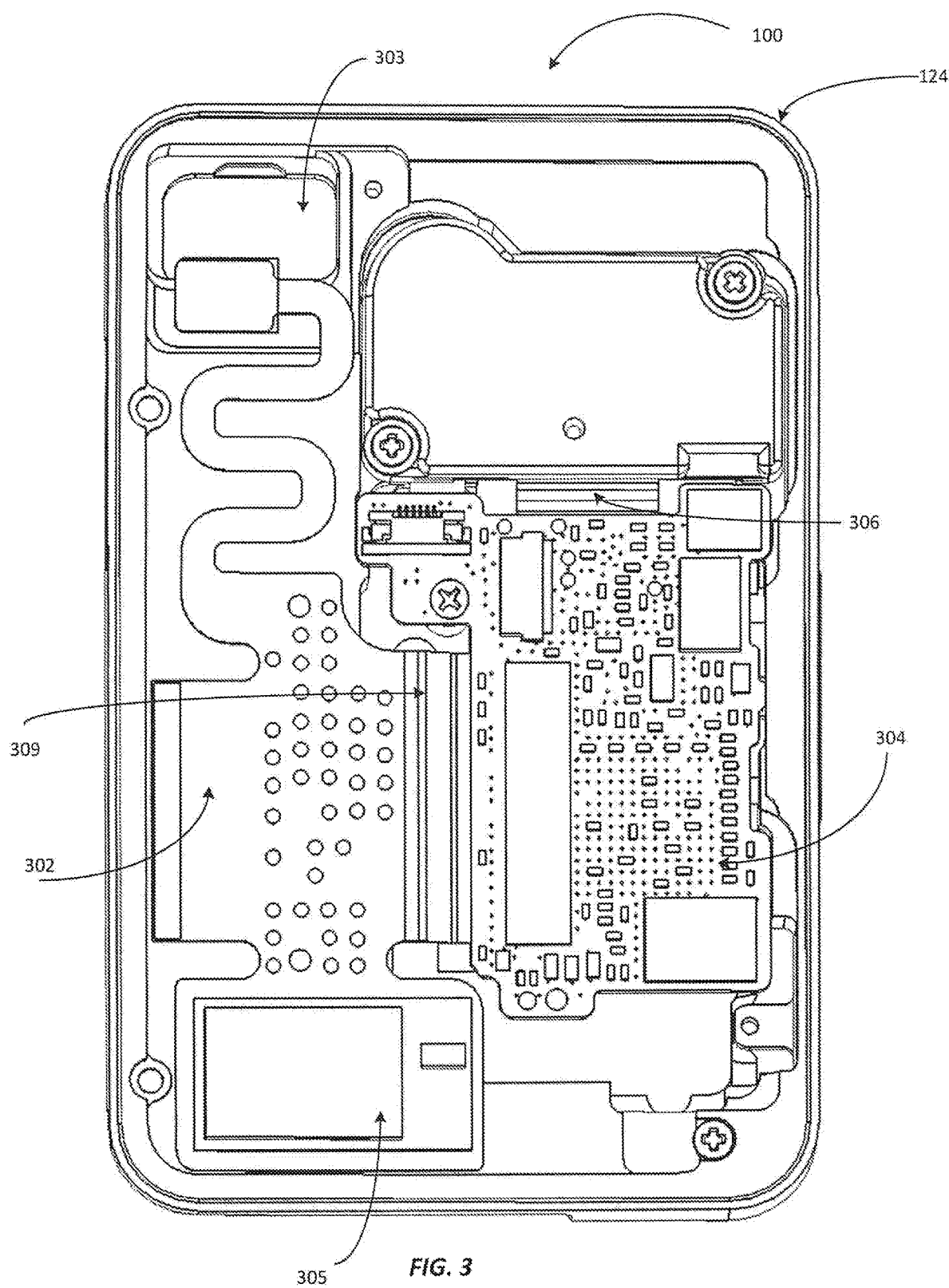
FIG. 3 is a schematic that depicts the circuitry and components of a portable medical device with the front side housing removed as in FIG. 1.

FIG. 3 provides a schematic representation of the device depicted in FIG. 1 with the front face of the housing 124 removed and the internal components exposed. As shown, the portable medical device 100 includes a printed circuit board (PCB) assembly including a flex serpentine board 302, a main board 304, a connector for the flex board and main board to direct current (DC) 306, a pressure board 303, and a connector for the flex board to the pressure board 309. Additionally, the device includes a Bluetooth PCB assembly 305 for short wave, such as radio frequency (RF) communication. Such communication can be useful if a user of the device wishes to transfer data to, for example, a Bluetooth-enabled mobile telephone, such as a Smart Phone.

Figure 4:
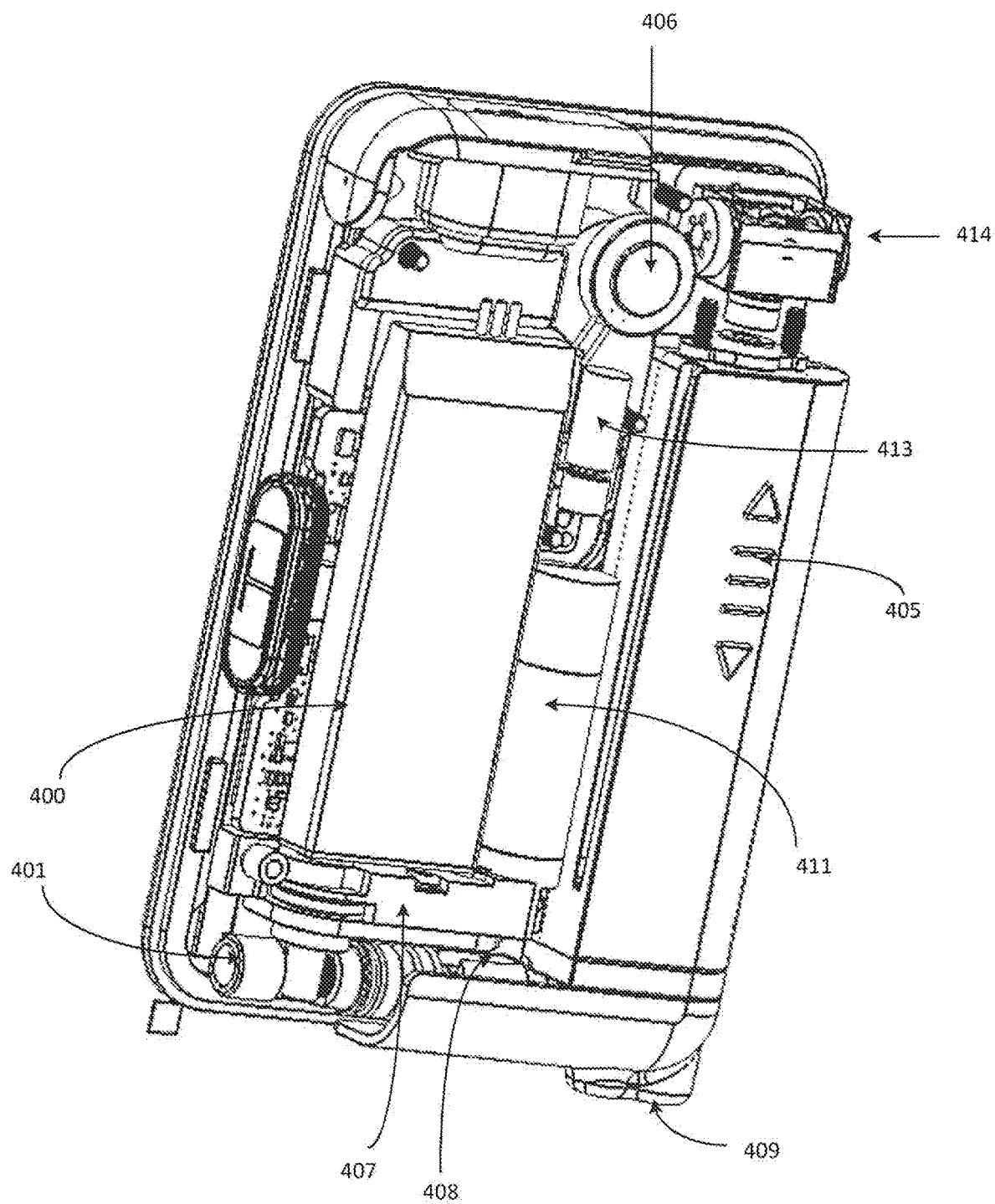
FIG. 4 is a schematic that depicts a perspective view of the device of FIG. 1, having the back face of the housing removed.

FIG. 4 is a schematic view of the back of the portable medical device in FIG. 1 with the rear face removed. As shown in FIG. 4, the various elements controlled by the PCB on the front schematic view in FIG. 3 are provided. The device can include a speaker 406 and vibrate mechanism 413 for providing alerts and other sounds indicating a function has been performed on the device. Additionally, the device can include a micro-valve assembly 414, including, for example, a venting system and a thermal leak platform for the insulin cartridge. The insulin cartridge can be covered by a cartridge door 405 and the housing of the portable medical device can include a cartridge shroud 409 in which the connecting tube 118 delivering the insulin to the patient may be inserted. Additionally, the device can include a power charging system, which receives the controlled current from the power isolation chip. The power charging system may be used to charge a power storage cell such as a rechargeable battery 400 of the portable medical device. Some embodiments may use a rechargeable battery such as a NiCad battery, LiPo battery or NiMH battery.

The device 100 comprises an infusion pump device, and therefore also includes a drive/pump element such as a pumping mechanism for delivery of fluid such as insulin to the connecting tube 118, as described above in connection with FIG. 1. In FIG. 4 several of the pump device components are depicted such as a pump motor 411, rack bushing 401, rack pushrod 408 and gear box 407. The device is not limited to these components and fewer or additional components may be employed depending upon the particular operating requirements of a device.

Figure 5:
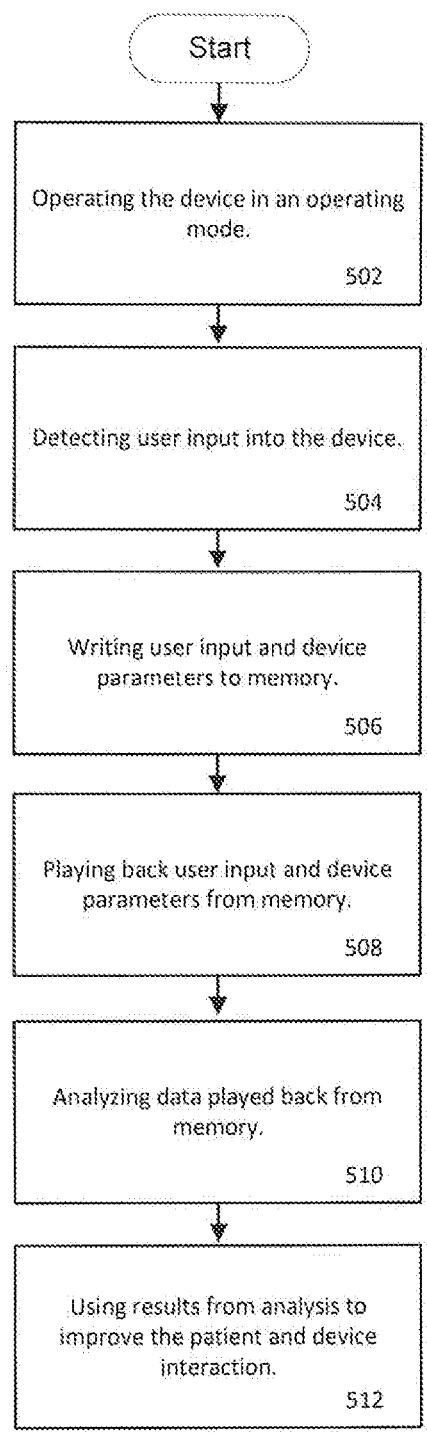
FIG. 5 is a flowchart showing an embodiment of the invention wherein there is an operating mode that provides a method to record all user interactions and allow the clinician to review the patient's performance for the initial use period.

FIG. 5 is a flowchart that illustrates a method of use of a device such as the devices 100, 600 described herein. The operations are performed such that all user interactions are detected and recorded. Such parameter detecting and memory writing features, as described previously, permit a user, caregiver, clinician, trainer, and the like to review the recorded user performance. After the portable medical device as described herein is attached to a patient, at the operation 502, the device is placed in operation. Next, at step 504, the user interacts with the device either through a button, a touchscreen, or other input mechanism. The user interaction may comprise, for example, selecting a function, providing an input or navigating through the user interface. In step 506 the device detects the user interaction and stores the user interaction, including any button press, touchscreen interaction, etc., in the device memory. Optionally, additional device parameters can be stored in memory, such as a timestamp for time of day, external sensor readings indicating body temperature, blood glucose level, blood pressure, glucose level data from a continuous glucose monitor and others, as described herein above. The recording can simply be a "snapshot" of the user input and selected device parameters at that particular time, or the device may take numerous sequential "snapshots" separated by a period of time. For a sequence of snapshots, the timestamp recorded with each interaction will indicate the passage of time between consecutive user interactions. Optionally the device may be programmed to continuously record data for a predetermined period of time after a first user interaction. Further, the device may be programmed with a continuous F.I.F.O. (first in first out) buffer that maintains a predetermined amount of data in memory and, upon user interaction, stores data starting at a predetermined period of time (e.g. initiated by the user) and continuing to 5 a period of time after the user interaction. Numerous other methods of capturing data are readily known by those of skill in the art.

In step 508 the stored data can be played back in a playback mode on the device itself, or the stored data can be transferred from device memory to a separate device, such as a computer, for playback. In step 510 the user interaction with the device can be analyzed for potential or actual errors. The analysis can be performed on a screen-by-screen basis or through analysis software that processes all the stored user interactions and provides an automatic summary of the patient's therapy. The analysis software may reside on an external device or may be installed at the device itself. The analysis operations of the software may be applied to stored or historical data. The analysis may be applied in real-time as the patient is operating the device, to provide an indication of how well the patient is operating the device. The automated analysis can identify "close calls" where the patient changes the therapy at the last moment, "difficulties" where the patient deviates significantly from an optimum path or "errors" where the patient initiates a therapy or setting that does not match the instructions of a trainer or caregiver. The analysis software may provide an indication of trending, that is, an evaluation of how well the patient is interacting with the user interface. It would be expected that patient performance in terms of errors would improve most greatly during an initial period and then would stabilize over time. If the system detects that the patient is regressing, such as an increase in observed errors, then the system may provide a notification of patient difficulty or regression. Other pertinent issues can readily be identified by the analysis software and are known to those of skill in the art. In step 512, the results of the analysis are used by the trainer, patient, clinician, caregiver or the like, to improve the user-device interaction. For example, improvement may be achieved by changing settings in the device, and/or providing additional training to the user.

The benefits of the parameter detecting and memory writing features during operation should be readily apparent as compared to a conventional training mode of operation. In a training mode, the device may not be coupled to the patient, or if coupled, may not be operational, and thus the user interaction scenarios are simulated and are likely not representative of that particular user's responses in a medicament delivery context. Complications can arise with medicament delivery devices such as insulin pumps because each individual user or patient responds uniquely to a given insulin dosage and rate of dosage. Additionally, each patient has a unique lifestyle, which may not be considered in the training mode. For instance, some patients have the ability to self-manage their dependency on insulin such as sensing when blood sugar is low and eating particular foods with carbohydrate levels and types adequate to safely increase their blood sugar levels. In such a scenario, the insulin delivery device may initiate therapy when it is not required, hence risking over-medication of the patient. Conversely, other patients may require significant dependence on insulin because of poor eating habits or the lack of the ability to self-manage their disease. In these scenarios the insulin delivery device may deliver too little insulin too late, thus risking under-medication of the patient.

Therefore the parameter detecting and memory writing features of operation described herein provide an individualized "fine tuning" or customization of the relationship between a patient and their device. This kind of fine tuning typically requires extensive support from trainers, clinicians, and/or other caregivers to interact with the patient on a frequent basis. However, with the ability of the device to capture user interactions along with the device parameters, the trainer, clinician and/or other caregiver can expediently identify and analyze only the relevant areas for improvement. Further, with automated analysis software, the trainer, clinician, and/or other caregiver can even more expediently identify the areas of concern and efficiently fine tune those particular areas of the user interaction. Thus, this method can effectively train patients, each with their unique circumstances and individualized response to therapy, how to efficaciously operate ambulatory medical devices while requiring reduced support from clinicians.

Although the aforementioned description specifically describes a portable medical device for administering insulin to a patient, it should be understood that such a device is only one embodiment of the invention. The device can also include any portable device having a display and a processor. For example, the device can include a mobile computing device, such as a Smartphone. In one embodiment, such a mobile computing device can function as a remote control for a portable medical device as described herein. Alternatively, a dedicated remote control specifically designed for use with a portable medical device can be used to control the device.

The methods, systems, and devices discussed above are intended merely to be examples. Various embodiments may omit, substitute, or add various procedures or components as appropriate. For example, it should be appreciated that, in alternative embodiments, the methods may be performed in an order different from that described, and various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in this description to provide a thorough understanding of the embodiments. Nevertheless, it will be understood by one of ordinary skill in the art that the embodiments may be practiced without these specific details. For example, well-known circuits, processes, algorithms, structures, and techniques have been shown without unnecessary detail in order to avoid obscuring the embodiments. Further, the headings provided herein are intended merely to aid in the clarity of the descriptions of various embodiments, and should not be construed as limiting the scope of the invention or the functionality of any part of the invention. For example, certain methods or components may be implemented as part of other methods or components, even though they are described under different headings.

It is noted that embodiments may have been described as a process that is depicted as a flow diagram or block diagram. Although each diagram may describe the process as a sequential series of operations, many of the operations can be performed in parallel or concurrently. In addition, the order of the operations may be rearranged. A process may have additional steps not included in the figures. Each operation of a process is performed or executed by the processor of the device.

The description above has been provided in terms of presently preferred embodiments so that an understanding of the present invention can be conveyed. There are, however, many configurations and techniques for data management systems that were not specifically described herein, but with which the present invention is applicable. The present invention should therefore not be seen as limited to the particular embodiments described herein, but rather, it should be understood that the present invention has wide applicability with respect to data management generally. All modifications, variations, or equivalent arrangements and implementations that are within the scope of the attached claims should therefore be considered within the scope of the invention.

The invention claimed is:

1. A method of improving a user's treatment of diabetes, comprising:
   receiving parameters relating to programming and operation of an ambulatory infusion pump;
   receiving glucose level data of the user;
   analyzing the parameters relating to the user's programming and operation of the ambulatory infusion pump and the glucose level data with automated analysis software in real-time as the user is operating the ambulatory infusion pump;
   identifying with the automated analysis software one or more trends in user operation of the device based on the analysis; and
   providing user-specific recommendations based on the user's lifestyle for improving treatment of the user based on the one or more trends.

2. The method of claim 1, wherein analyzing the parameters relating to programming and operation of the ambulatory infusion pump includes analyzing insulin dosages delivered to the user.

3. The method of claim 1, wherein the automated analysis software further analyzes data relating to a physical state of the user in identifying the one or more trends.

4. The method of claim 1, wherein receiving glucose level data of the user includes receiving the glucose level data from a continuous glucose monitor.

5. The method of claim 1, wherein providing user-specific recommendations for improving treatment of the user based on the one or more trends includes providing the user-specific recommendations on a display.

6. The method of claim 5, wherein providing the user-specific recommendations on a display includes providing the recommendations on a display of a smartphone.

7. The method of claim 1, further comprising transferring the parameters relating to the user's programming and operation of the ambulatory infusion pump and the glucose level data to a separate device and wherein the automated analysis software resides on the separate device.

8. The method of claim 1, wherein the one or more trends in user operation of the device identified based on the analysis includes one or more errors where user operation does not match caregiver instructions.

9. The method of claim 1, wherein the one or more trends in user operation of the device identified based on the analysis includes one or more difficulties where user operation deviates significantly from an optimum path for operation of the ambulatory infusion pump.

10. The method of claim 1, wherein the user-specific recommendations for improving treatment of the user based on the one or more trends include recommendations for changing settings of the ambulatory infusion pump.

11. A method of improving a user's treatment of diabetes, comprising:
receiving information pertaining to a user's treatment of diabetes, the information including glucose levels of the user;
analyzing the information pertaining to the user's treatment of diabetes with automated analysis software in real-time as the information pertaining to the user's treatment of diabetes is received;
identifying with the automated analysis software one or more areas where the user can improve treatment of the user based on the analysis; and
providing user-specific recommendations based on the user's lifestyle for improving treatment of the user based on the one or more areas.

12. The method of claim 11, wherein the automated analysis software further analyzes insulin dosages delivered to the user in identifying the one or more areas where the user can improve treatment of the user.

13. The method of claim 11, wherein the automated analysis software further analyzes data relating to a physical state of the user in identifying the one or more areas where the user can improve treatment of the user.

14. The method of claim 11, further comprising receiving the glucose levels of the user from a continuous glucose monitor.

15. The method of claim 11, wherein providing user-specific recommendations for improving treatment of the user based on the one or more areas includes providing the user-specific recommendations on a display.

16. The method of claim 15, wherein providing the user-specific recommendations on a display includes providing the recommendations on a display of a smartphone.

17. The method of claim 11, further comprising transferring the information pertaining to the user's treatment of diabetes to a separate device and wherein the automated analysis software resides on the separate device.

18. The method of claim 11, wherein the one or more areas where the user can improve treatment identified based on the analysis includes one or more errors where user operation does not match caregiver instructions.

19. The method of claim 11, wherein the one or more areas where the user can improve treatment identified based on the analysis includes one or more difficulties where user operation deviates significantly from an optimum path for operation of the ambulatory infusion pump.

20. The method of claim 11, wherein the user-specific recommendations for improving treatment of the user based on the one or more areas include recommendations for changing settings of an ambulatory infusion pump.

\* \* \* \* \*